United States Patent
Alphonse et al.

(10) Patent No.: US 7,852,485 B2
(45) Date of Patent: Dec. 14, 2010

(54) SINGLE TRACE MULTI-CHANNEL LOW COHERENCE INTERFEROMETRIC SENSOR

(75) Inventors: Gerard A. Alphonse, Princeton, NJ (US); Donald B. Carlin, Pennington, NJ (US); Fred Rappaport, Jamison, PA (US)

(73) Assignee: Medeikon Corporation, Ewing, NJ (US)

( * ) Notice: Subject to any disclaimer, the term of this patent is extended or adjusted under 35 U.S.C. 154(b) by 288 days.

(21) Appl. No.: 12/194,713

(22) Filed: Aug. 20, 2008

(65) Prior Publication Data

US 2010/0053632 A1 Mar. 4, 2010

Related U.S. Application Data

(62) Division of application No. 10/988,115, filed on Nov. 12, 2004, now Pat. No. 7,417,740.

(51) Int. Cl.
*G01B 9/02* (2006.01)
*G01B 11/02* (2006.01)
(52) U.S. Cl. .................. 356/479; 356/497; 356/492
(58) Field of Classification Search ............. 356/479, 356/478, 497, 491, 492, 495
See application file for complete search history.

(56) References Cited

U.S. PATENT DOCUMENTS

| 4,697,926 | A | * | 10/1987 | Youngquist et al. ......... 356/478 |
|---|---|---|---|---|
| 5,173,743 | A | * | 12/1992 | Kim ........................ 356/478 |
| 7,184,148 | B2 | * | 2/2007 | Alphonse ................. 356/479 |
| 7,190,464 | B2 | * | 3/2007 | Alphonse ................. 356/479 |
| 7,242,480 | B2 | * | 7/2007 | Alphonse ................. 356/479 |
| 7,242,832 | B2 | * | 7/2007 | Carlin et al. .............. 385/116 |
| 7,327,463 | B2 | * | 2/2008 | Alphonse ................. 356/479 |
| 7,417,740 | B2 | * | 8/2008 | Alphonse et al. .......... 356/479 |
| 7,474,408 | B2 | * | 1/2009 | Alphonse ................. 356/479 |
| 2005/0057756 | A1 | * | 3/2005 | Fang-Yen et al. .......... 356/497 |
| 2005/0105097 | A1 | * | 5/2005 | Fang-Yen et al. .......... 356/497 |
| 2005/0254057 | A1 | * | 11/2005 | Alphonse ................. 356/479 |
| 2005/0254058 | A1 | * | 11/2005 | Alphonse ................. 356/479 |
| 2005/0254059 | A1 | * | 11/2005 | Alphonse ................. 356/479 |
| 2005/0254060 | A1 | * | 11/2005 | Alphonse ................. 356/479 |
| 2005/0254061 | A1 | * | 11/2005 | Alphonse ................. 356/479 |
| 2006/0103850 | A1 | * | 5/2006 | Alphonse et al. .......... 356/479 |
| 2007/0285669 | A1 | * | 12/2007 | Ajgaonkar et al. ......... 356/482 |
| 2010/0039651 | A1 | * | 2/2010 | Gelikonov et al. ......... 356/479 |
| 2010/0053632 | A1 | * | 3/2010 | Alphonse et al. .......... 356/479 |

* cited by examiner

*Primary Examiner*—Patrick J Connolly
(74) *Attorney, Agent, or Firm*—Pepper Hamilton LLP

(57) ABSTRACT

Interferometers and autocorrelator based sensors are disclosed that are configured to have multiple sample arms which can be scanned and the backscattered low coherence source light from a sample resolved in a single sweep of one or more variable delays of the sensor. Borescopes and catheters capable of scanning multiple sections or areas of materials and tissues using these sensors are described.

18 Claims, 15 Drawing Sheets

SINGLE TRACE MULTI-CHANNEL LOW COHERENCE INTERFEROMETRIC SENSOR

BACKGROUND AND SUMMARY

In various fields of medicine and engineering it is often necessary to inspect surfaces that are difficult to reach. For example engine cylinders, compressors for jet aircraft engines, heat exchangers, internal organs, cavities, and arterial passageways in a patient. Biomedical imaging technology, for example, magnetic resonance imaging, X-ray computed tomography, ultrasound, and confocal microscopy can be used to inspect and characterize a variety of tissues and organs. However, there are many situations where existing biomedical diagnostics are not adequate. This is particularly true where high resolution, about 1 micron, imaging is required. Resolution at this level often requires biopsy and histopathologic examination. While such examinations are among the most powerful medical diagnostic techniques, they are invasive and can be time consuming and costly. Furthermore, in many situations conventional excisional biopsy is not possible. Coronary artery disease, a leading cause of morbidity and mortality, is one important example of a disease where conventional diagnostic excisional biopsy can not be performed. There are many other examples where biopsy can not be performed or conventional imaging techniques lack the sensitivity and resolution for definitive diagnosis.

A borescope is an optical device such as a prism or optical fiber that can be used to inspect inaccessible spaces. An endoscope is an instrument for visualizing the interior of a hollow organ like a colon or esophagus. The observed part of the internal surface can be illuminated with the help of the illumination channel and the optical observation system allows investigation of the internal space surface. During inspection it may be advantageous and important to investigate lateral surface in the space.

Elements allowing a change in the direction of optical observation permit inspection inside spaces and lateral surfaces that a rigid borescope or endoscope cannot view. Endoscopes and borescopes can include a means of articulating the tip of the scope so that it bends in several directions to look around a cavity. However, in many applications, for example arteries, there is insufficient room in the cavity or conduit for articulation of the scope tip.

Rather than being flexible, a rigid endoscope can contain a mount, an optical system for observation, and a light guide. The mount and the light guide can be placed in a tube housing. The optical axes of the observation and illumination system for lateral direction are deflected at an angle with respect to the lens optical axis with the help of a prism. In order to observe the entire lateral surface along the whole transverse perimeter of the investigated cavity, it is necessary to rotate the entire endoscope housing around the axis of symmetry. Fiber optic inspection devices may contains a lens in a mount and illumination lamps installed in a housing in a lateral wall of the housing in which a window is provided. Lateral observation can be performed due to a reflection prism situated opposite the window. For panoramic observation of the walls in a space the entire housing needs to be rotated. In some instruments the illumination source must also be rotated complicating the design and operation of such a device.

Current methods for screening and diagnosis of pathologic conditions in tissue such as cancer often involve surgical biopsy of the tissue followed by histological evaluation. This procedure is not only invasive, time-consuming and expensive but often is not capable of rapid and reliable screening of a large surface such as the colon, esophagus, or stomach. Since early diagnosis and treatment tend to be critical to effective and successful treatment of these pathologies, the development of better techniques and devices for diagnosis and screening would result in improved clinical outcomes.

Optical coherence tomography (OCT) is an imaging technique which allows high resolution observation and characterization of tissue microstructure imaging with resolution on the order of microns. This technique measures detailed changes within a few millimeters of a non-transparent tissue structure. One drawback of the OCT imaging is the time required to obtain images over a sufficient area.

Optical coherence domain reflectometry ("OCDR") is an optical technique that uses a scanning Michelson interferometer in conjunction with a broadband illuminating source and cross-correlation detection. The similar technique of optical coherence tomography ("OCT") can be used for imaging with catheters.

Both OCDR and OCT use optical data collected by a single mode optical fiber to determine the morphology, physical properties and location of various types of interspersed materials or biological tissue. Typically a probe used in conjunction with either OCDR and OCT includes an optical fiber having a head at its distal tip. Alternatively, the probe is formed by inserting an optical fiber concentrically into a thin-wall flexible hypodermic stainless-steel tube and fastening it with cement. A window in the tube allows light to pass to and from the head at the tip of the optical fiber. The probe is then inserted into the tissue or organ to be examined. Light emitted by the head of the optical fiber is reflected from the adjacent body of tissue or organ. The head then collects the reflected light, also known as "back-scattered" light.

Using a Michelson interferometer in conjunction with this apparatus the morphology, properties and location of the various materials, tissue or organ elements that caused the back-scattered light are determined and an image generated to provide a real-time visual display of the device, body of tissue, or organ being examined.

However, as a typical optical fiber can only emit light and gather back-scattered light along its axial centerline, it is limited to viewing straight ahead. A view transverse to the axial centerline of the fiber can be obtained by turning or bending the head of the fiber perpendicular to its axial centerline, and this is often very difficult or even impossible in the close confines typically encountered during surgical procedures, or in examining the sides of an artery or vein.

Mounting a gradient refractive index lens or a mirrored corner cube on the head of the optical fiber can be used to obtain lateral scans. Both a gradient refractive index lens or a mirrored corner cube deflect the emitted light at an angle transverse to the axial centerline of the optical fiber, and thus provide for lateral viewing. However, these apparatus add bulk to the head of the optical fiber. For example, the diameter of an optical fiber typically used in conjunction with OCDR and OCT is on the order of about 90 microns, while the diameter of the smallest GRIN lens is about 150 microns and that of the smallest mirrored corner cube is about 125 microns. The use of either of the aforementioned optical devices thus renders some locations inaccessible and makes the optical fiber more difficult to maneuver. In addition, extremely small GRIN lenses and mirrored corner cubes are quite expensive, and very fragile. Their use thus adds to the cost of the probe, and renders it prone to malfunction.

Embodiments of the present invention are devices that include two or more sample arms and one or more variable delay reference arms, the distal ends of the sample arms collecting source light backscattered from a sample. The backscattered light collected by the distal end of each sample or sensing arm is combined with reference light and low coherence interferometric signals for each sample arm produced in a single sweep of a variable delay of the device. The interference signal produced by the interaction of reference light and backscattered light for each sample arm is measured by a detector. Optionally the one or more sample arms have an adjustable delay. The devices of the present invention may be used to characterize a material using of low coherence light backscattered from the sample. These devices eliminate the need for optical switches or rotatable structures to sequentially address independent sample arms and permit the collection of low coherence source light backscattered from several different samples or from several different locations on a single sample utilizing a single sweep of one or more adjustable delays. The interference signals from device provides information on multiple surfaces of a sample and can be used to discriminate between healthy and diseased tissue without the need for rotating the probe or translating mirrors within the probe.

In one version of the device, two or more sensing or sample arms of an interferometer are coupled to one or more reference arms. The device can be used to obtain the low coherence interferometric (LCI) signals from all of the sample arms in a single long trace or sweep of one or more reference arms; each reference arm has a variable or adjustable delay. Optionally the sample arms may include an adjustable delay. The intensity of interference between the backscattered light from the sample and light from the reference section can be measured by a detector coupled to the reference arms and sample arms.

Another version the device is a sensor that includes two or more sensing arms, and a reference section with two or more arms where each reference arm has an adjustable delay. The sensing arms and the reference arm section are capable of being coupled to one or more low coherence light sources. The reference section and sample arms are configured to resolve interference of backscattered light and reference light from the two or more sensing arms in a single trace or sweep of the variable delay of the reference section. Optionally each sensing arms has an adjustable delay. The sample and reference arms can be configured in a relationship that permits acquisition of backscattering information from a sample and that can be used to improve signal averaging and noise reduction.

In another version of the device, two or more combined reference and sensing arms or probes of an autocorrelator are coupled with a delay compensator having a variable delay. LCI signals from interference between backscatter light collected by the probes and reference light from the probes can be separated or resolved during a single sweep of the delay compensator. The probe and delay compensator can be configured in a relationship that permits acquisition of backscattering information from a sample and that can be used to improve signal averaging and noise reduction. Optionally, each probe arm has an adjustable delay. The intensity of interference between the backscattered light and reference light can be measured by a detector coupled to the delay compensator section.

The devices of the present invention may include one or more low coherence light sources or they can be coupled to one or more exchangeable or pre-existing low coherence light sources. Optionally, the devices may be used for monitoring and delivering photodynamic therapy to a tissue. An activating light source may be coupled into the sample or probe arms of the devices for photodynamic therapy of a tissue. The sensor device may include a detector or it can be connected to an existing detector to measure the intensity of interference between the reference section light and backscattered light. The detector can include or may be connected to a processor that provides an output proportional to the interference between the backscattered light and reference arm light for each sensing or sample arm.

The sensors and apparatus in various versions of the invention can be included in a variety of inspection devices including but not limited to a borescope, endoscope, or catheter probe where the interference signals from the sensor provide simultaneously, information on the surface of the of the sample, and more preferable the sensor can discriminate between healthy and diseased tissue For example, an apparatus can include a guidewire, two or more light propagating probes in proximity, such as surrounding or being enclosed by, the guidewire. The probes propagate low coherence source light from a coupler or circulator into the sample and propagate backscattered light from the sample back to the coupler or circulator. The probes are coupled to interferometer or delay compensator that permits resolution of low coherence interferometric signals from one or more of the probes in a single scan of the adjustable delay in the compensator. An optical head that can direct source light to the sample in a variety of directions can be positioned on the distal end of the device; the optical head also collects backscattered light from the sample.

The device can include probes that guide or propagate light and may include waveguides, optical fibers, or a combination of these. In addition the probes can include an internal reflector. In a various embodiments the reference arm or delay arms are located along with the detector and processor separately (remotely) from the sample or probe arms.

The various sensors and apparatus of the invention can be used to characterize objects, tissues, and material samples. The method includes contacting the material(s) with a sensor having two or more probe or sample arms. Each probe arm of the sensor can have an adjustable delay, the probe arms and reference section or interferometer coupled together and configured such that an interference between backscattered source light from the sample for two or more probe arms and reference light are resolved during a single trace of one or more variable delays of the device. Interference between backscattered source light from each probe arm and reference section light in a single trace of the reference arm is used to characterize the material.

Preferably the low coherence interferometric signals from the two or more sample or probe arm are separated from each other by an amount that permits at least partial sampling of a material or tissue into two or more areas or regions. Preferably there is complete separation of the low coherence interferometric signals from each of the sample or probe arms, however incomplete resolution may also be useful in characterizing a material. In one embodiment, the interference detected for each of the two or more probes provides a characterization of the material. For example the interference may be used to characterize the repair of damaged tissue following surgery, the detection of a disease state of a tissue, or the presence of debris in a compressor or conduit. A preferred version of the invention is to use the apparatus to detect vulnerable plaque in a patient.

Because the devices of the present invention are capable of resolving low coherence interferometric signals that result from backscattered light collected by multiple sample arms in a single trace of an adjustable delay, the invention advantageously eliminates the need for optical switches to resolve LCI signals from multiple sample arms and eliminates the need for the use of multiple interferometers. In applications requiring the collection of several LCI traces in a short period of time, either from a single region or from several regions or directions, the collection of multiple information in a single trace will reduce the time for data collection and interpretation. For example, in probing the circumference of an artery, a single trace will enable rapid identification of a radial position with vulnerable plaque as compared with healthy tissue, and enable selection of probing regions along that radial position only. The identification can be done by comparing the various components of a trace, addition and or subtraction, to quickly determine differences, common features, and provide diagnosis.

Because the sample arms and probe arms, as well as reference arms and delay compensators in versions of the invention can be coupled to existing low coherence light sources, detectors, and processors, the fabrication of removable, interchangeable, or configurable sensor devices is possible.

FIGURES

Figure 4:
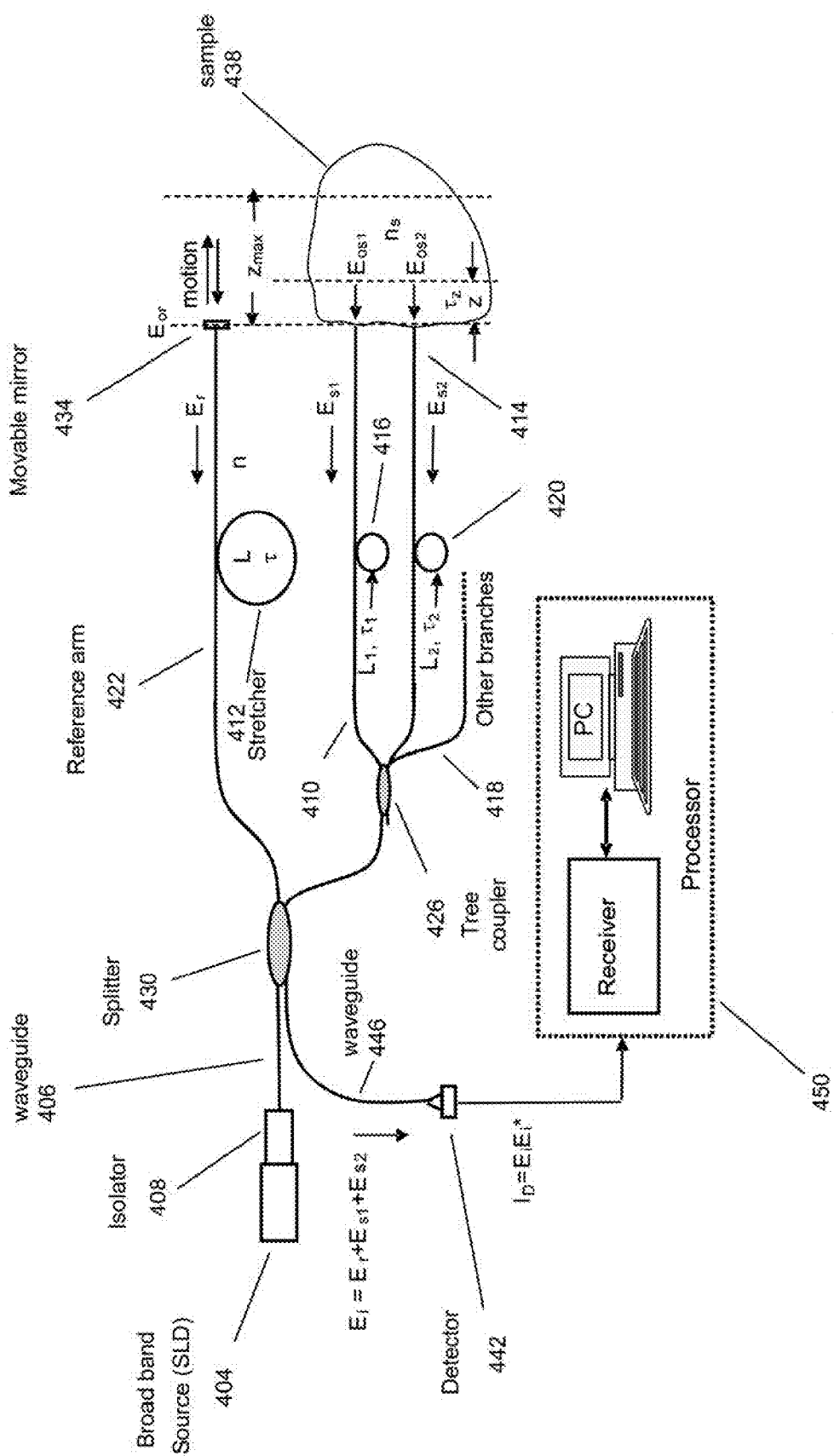
Figure 5:
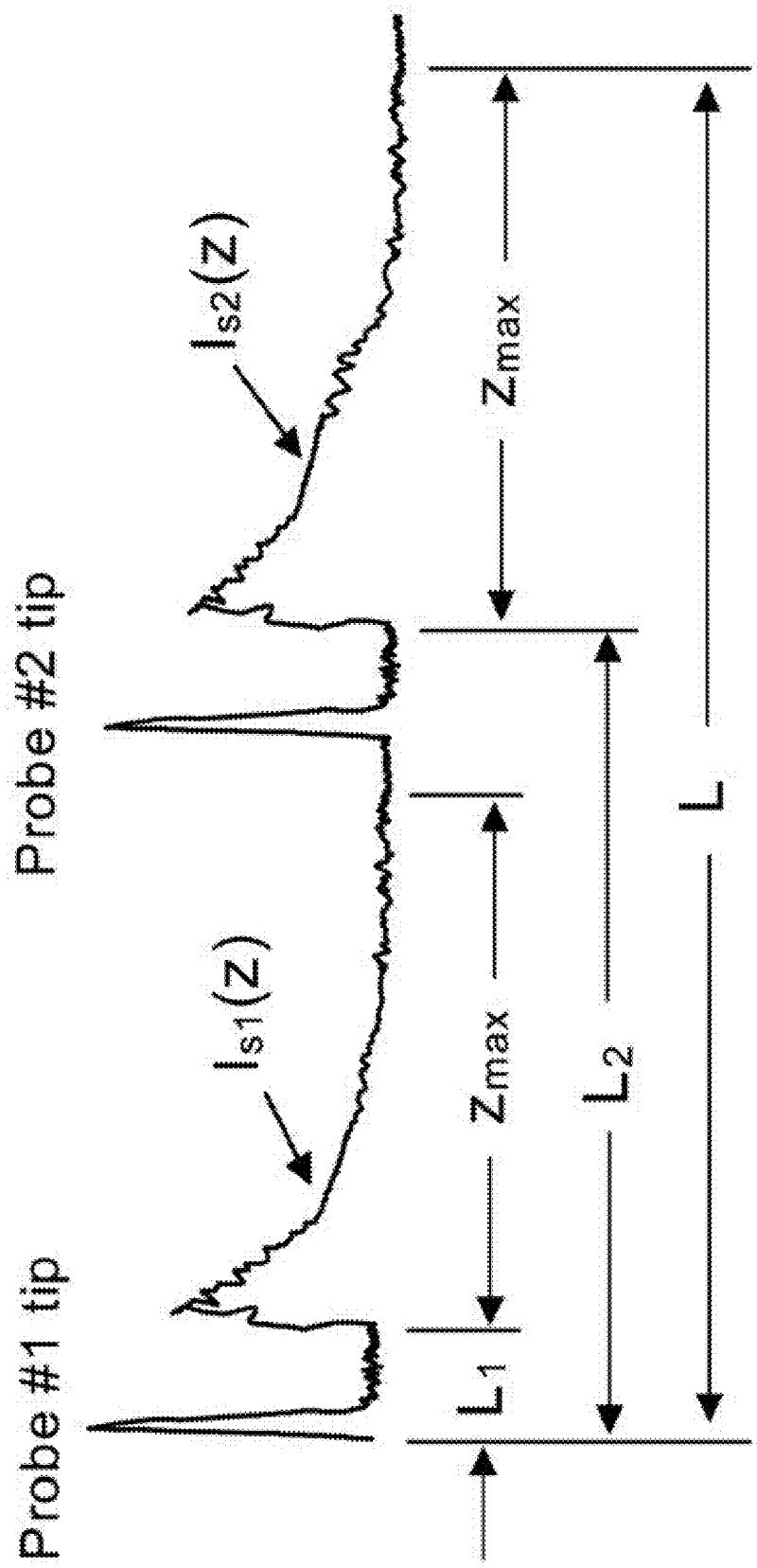

FIG. 4 Is an illustration of a Michelson based interferometer with multiple adjustable delay sensing arms whose interference with reference arm light can be resolved in a single trace of the reference arm variable delay, the sensing arms are shown in contact with a sample material having index of refraction $n_s$ and light penetration z, the multiple-arm probe can be joined together by means of the tree coupler;

FIG. 5 Is an example of a interference signal trace showing the relation among the various delays elements ($L_1$, $L_2$, $z_{max}$) used to resolve the various interference signals $I_{1s}(z)$, $I_{2s}(z)$ and other LCI components of a multiprobe system.

Figure 6:
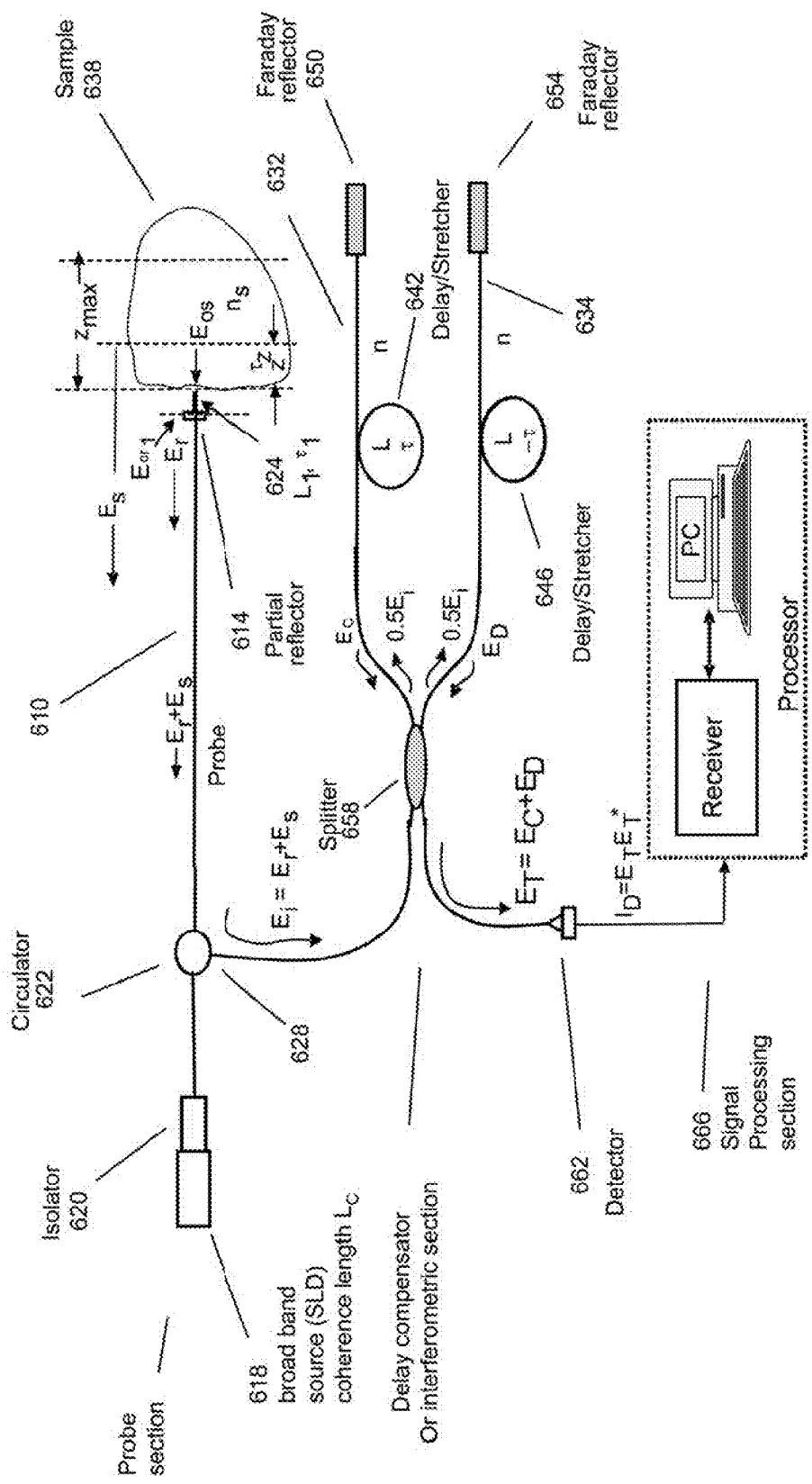

FIG. 6 Illustrates an autocorrelator where each waveguide or probe provides both the reference signal and the backscattered signal. The reference signal is a portion of the source light reflected light from the partial reflector, and the backscattered signal is the light transmitted through $L_1$ and recaptured at the tip of $L_1$ after backscattering from the sample. The portion of the probe on the left of the partial reflector carries both the reference and backscattered lights traveling backward toward the circulator. The delay between the reference and backscattered light is normally much larger than the coherence length of the light source, and the two do not interfere. The delay compensator has a variable delay that is used to make up for the reference/backscatter delay and bring the two under the coherence gate.

Figure 7:
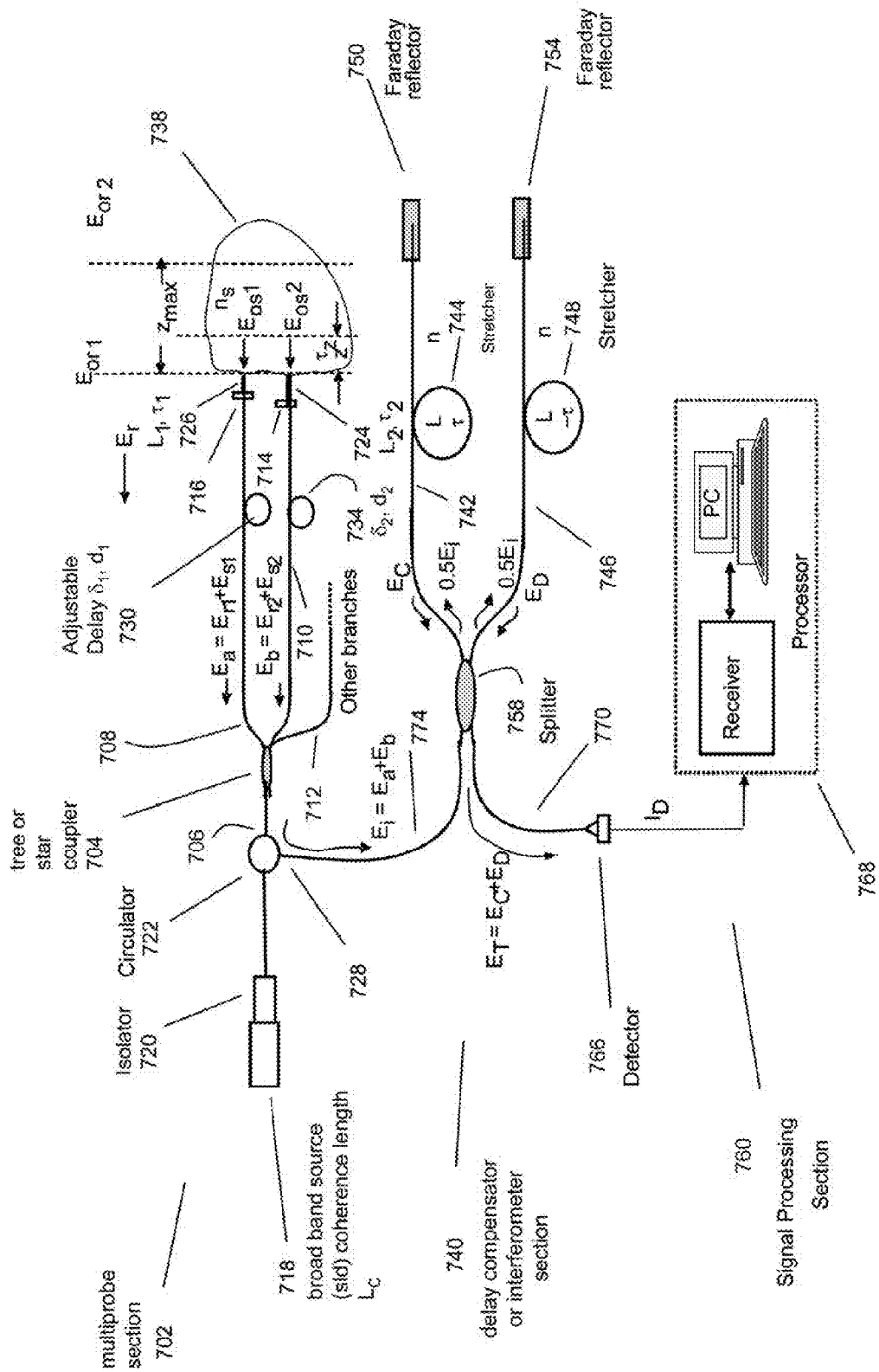

FIG. 7 Illustrates a version of the invention including two or more probes arms capable of being coupled to a low coherence light source, each probe arm propagating reference light and propagating backscattered light from the sample, each probe partially reflecting the source light. The device includes a delay compensator or interferometer section having two arms that receives reference and backscattered light from the probe arms. The delay compensator has polarization maintaining reflectors and a variable delay for each of the arms that is capable of bringing interference between the reference light and backscattered light (brings the reference and backscattered light to within the coherence length of the light source); the two or more partially reflecting probes are shown with an optional adjustable delay and are illustrated in contact with a sample, the probe arms are coupled through a circulator with polarization maintaining adjustable delay arms.

Figure 8:
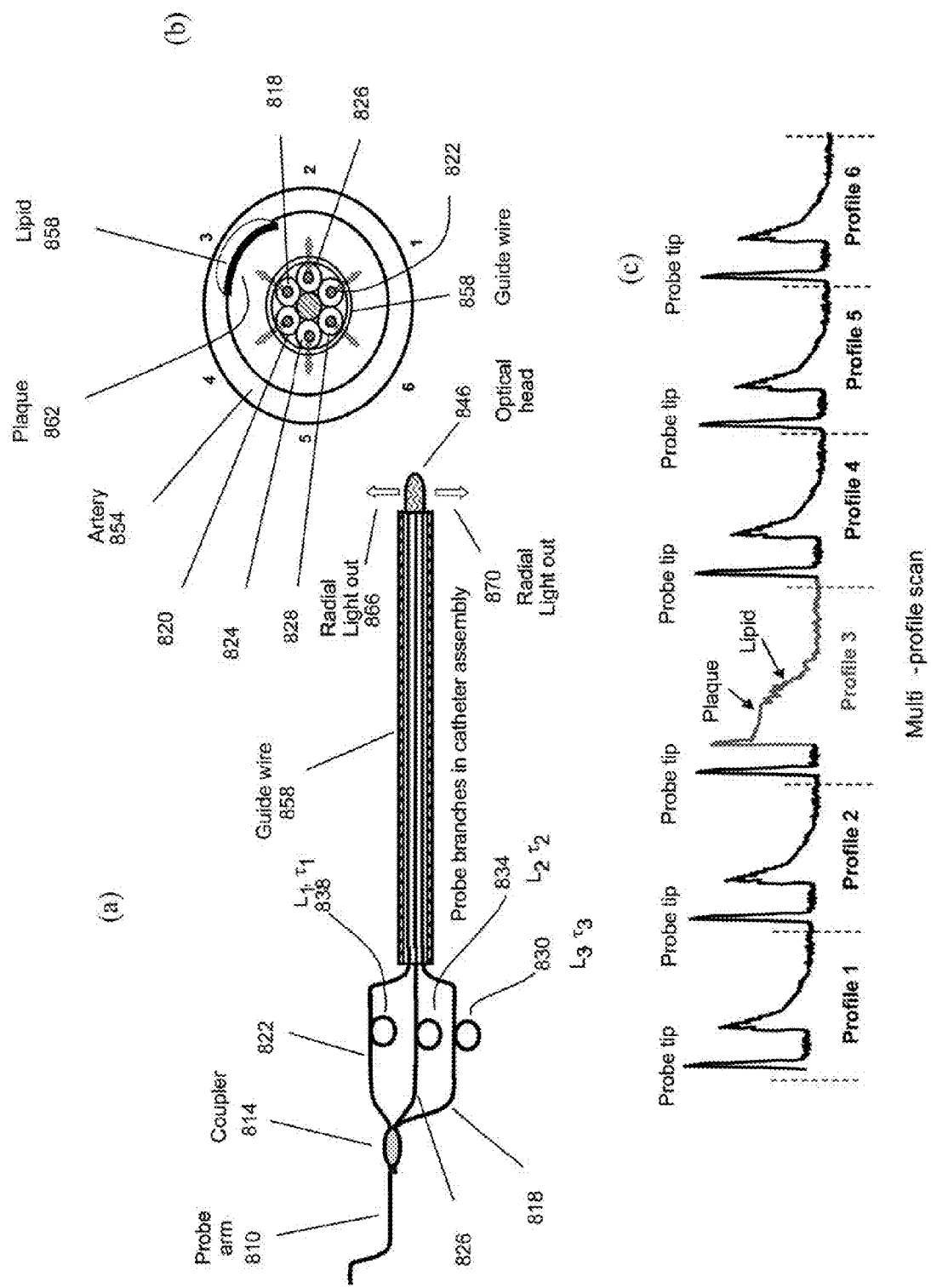

FIG. 8 (*a*) illustrates a side view of a multiple-branch catheter probe having a biocompatible guide wire enclosing one or more probes, FIG. 8(*b*) illustrates a cross section of the multiple catheter probe of (a) showing six waveguides or heads, and FIG. 8(*c*) depicts a trace illustrating the detection of a vulnerable plaque by one of the probes, (probe (3) shown in FIG. 8 (*b*)).

Figure 9:
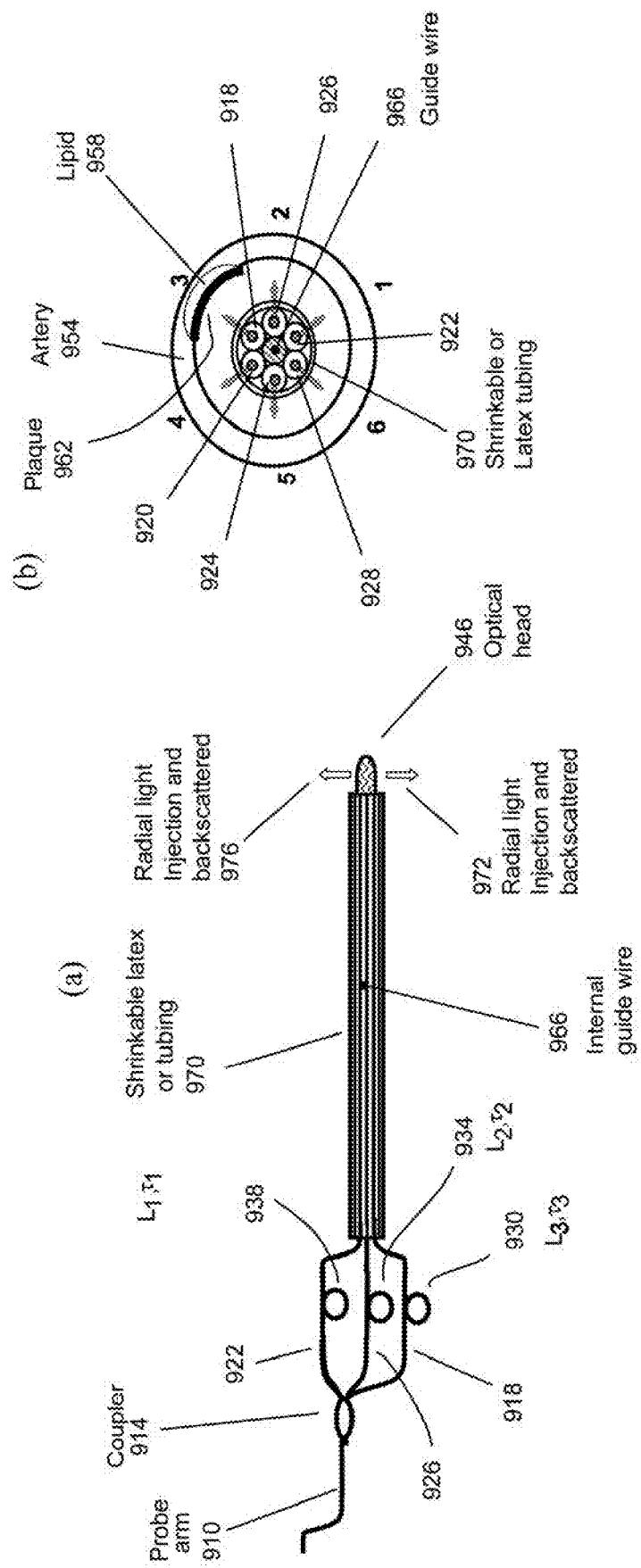

FIG. 9 (*a*) illustrates a side view of a multiple branch catheter probe where the probes surround all or a portion of the guide wire; FIG. 9(*b*) illustrates a cross section view of the assembly in (a) having the thin guide wire inside the probe fiber bundle and further illustrating the use a heat-shrinkable latex or other biocompatible tubing around the probe bundle.

Figure 10:
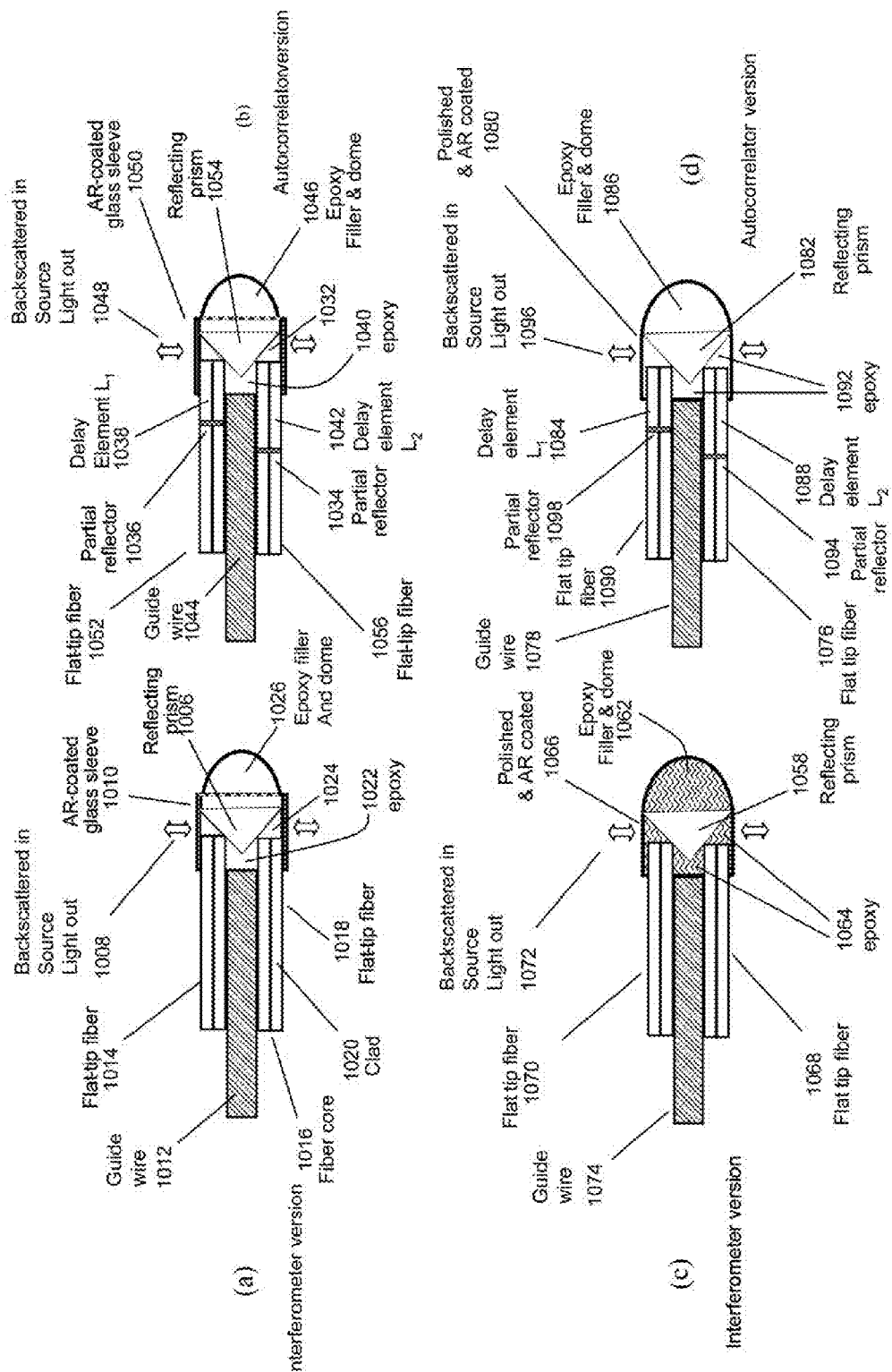
Figure 11:
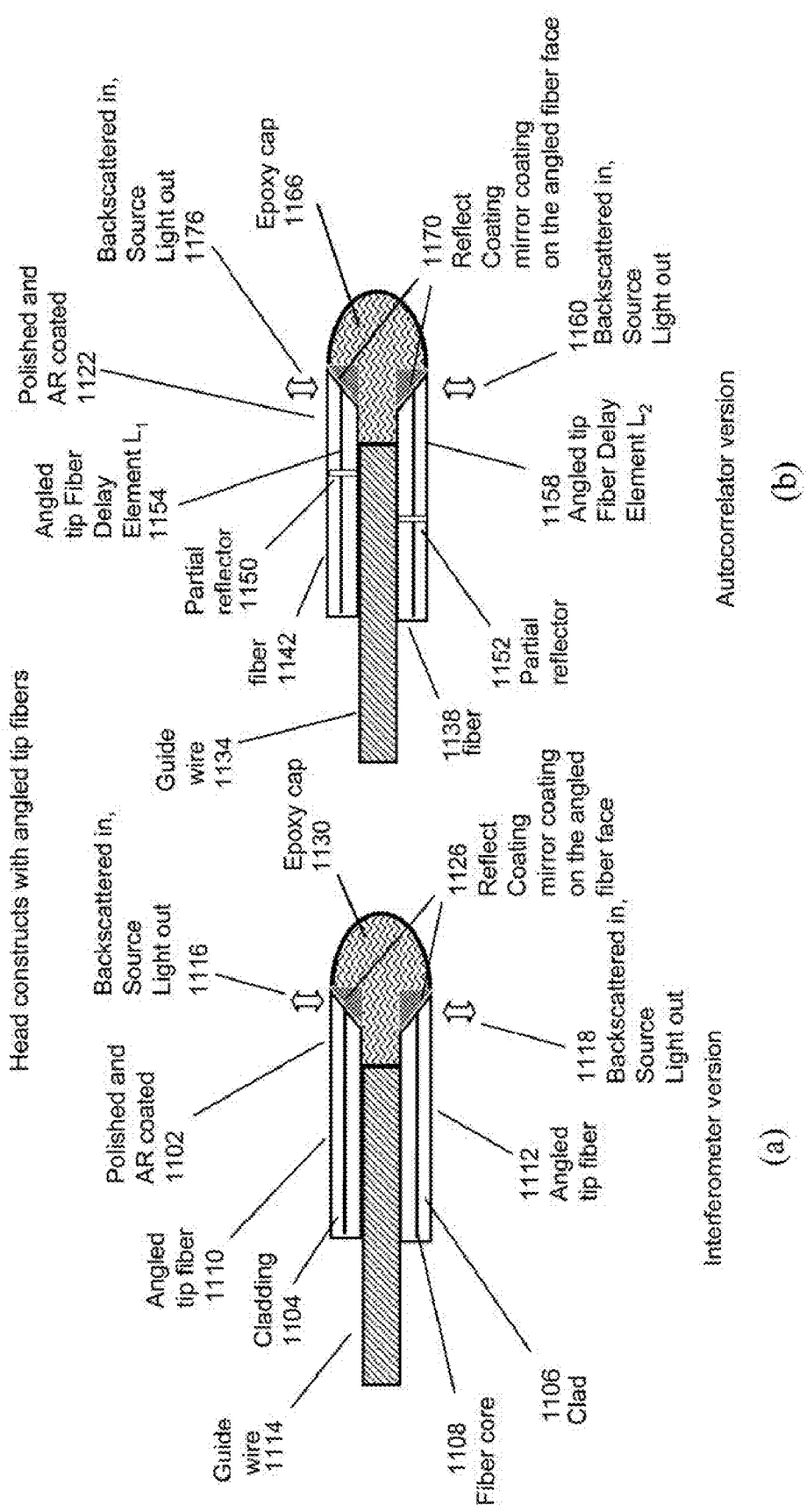

FIG. 10(*a-d*) illustrate various catheter head designs for interferometers and autocorrelators using flat-tip fibers and prism reflectors;

FIG. 11 Illustrates head design for interferometer (a) and autocorrelator (b) using angled-tip fibers.

Figure 12:
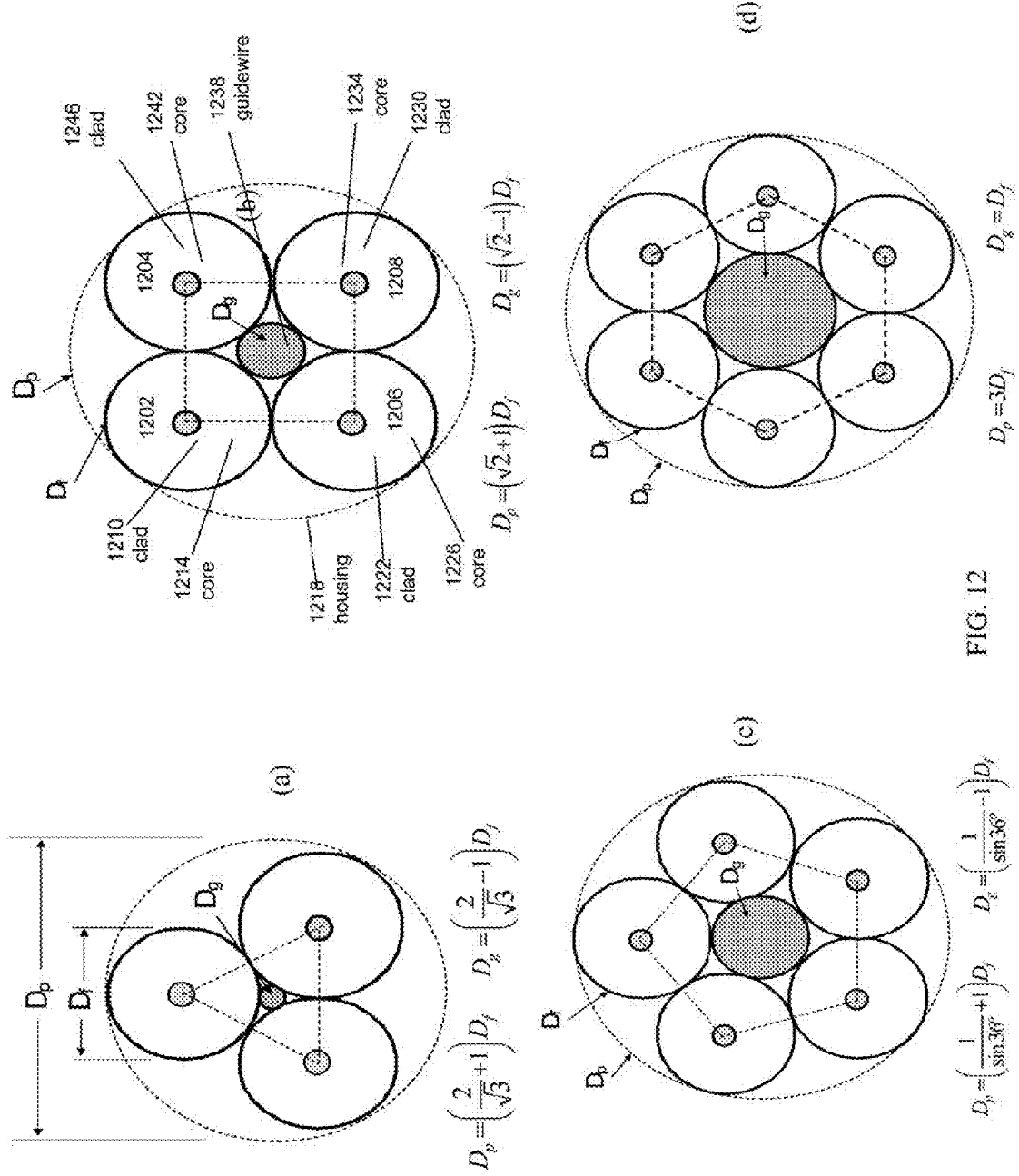

FIG. 12 (*a-d*) illustrate various non-limiting configurations for probes containing three to six fiber branches.

Figure 13:
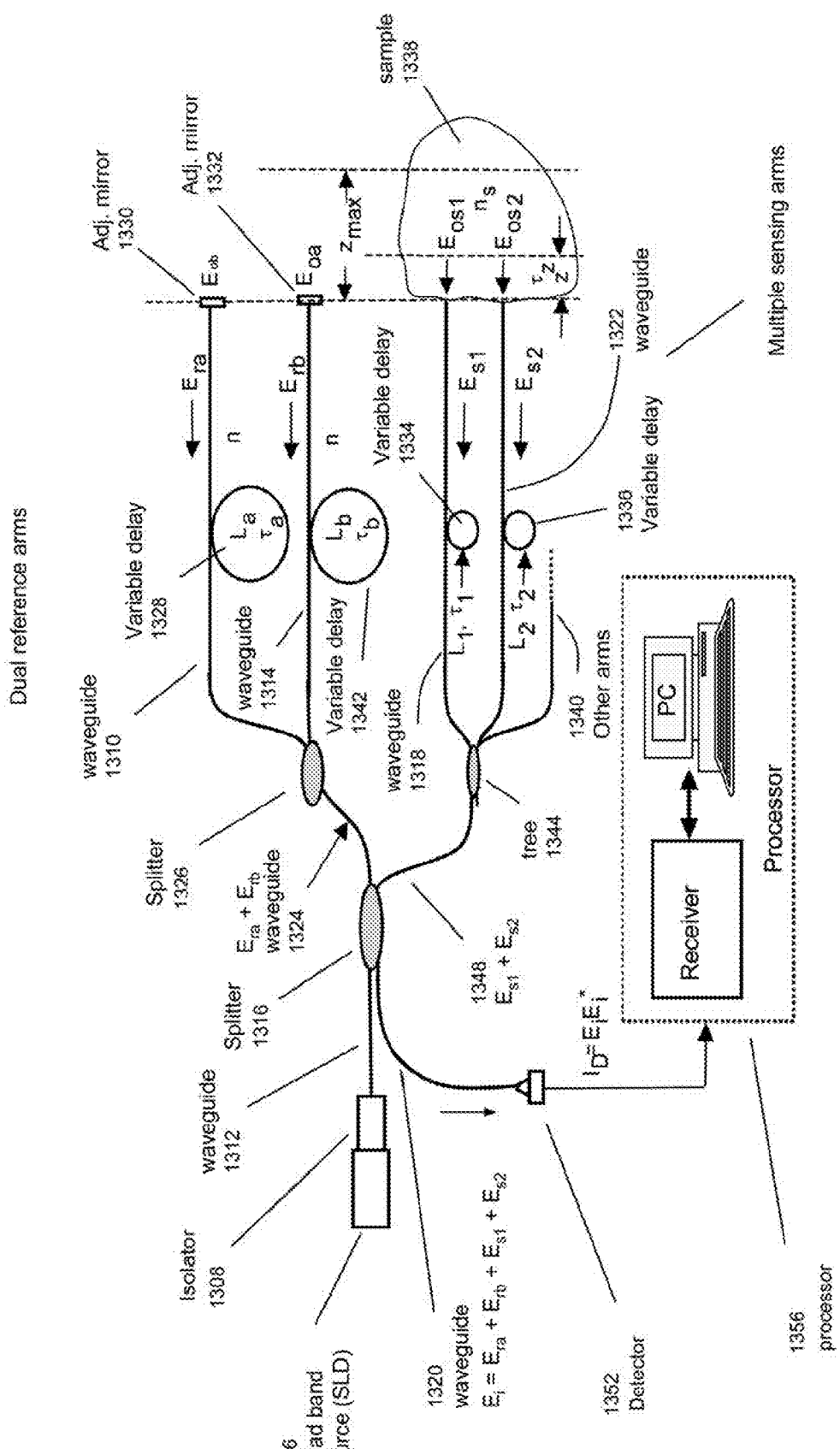

FIG. 13. Illustrates a dual reference arm embodiment of a multiple probe interferometer. The multiple reference arms may be used to achieve LCI signal averaging and noise reduction.

Figure 14:
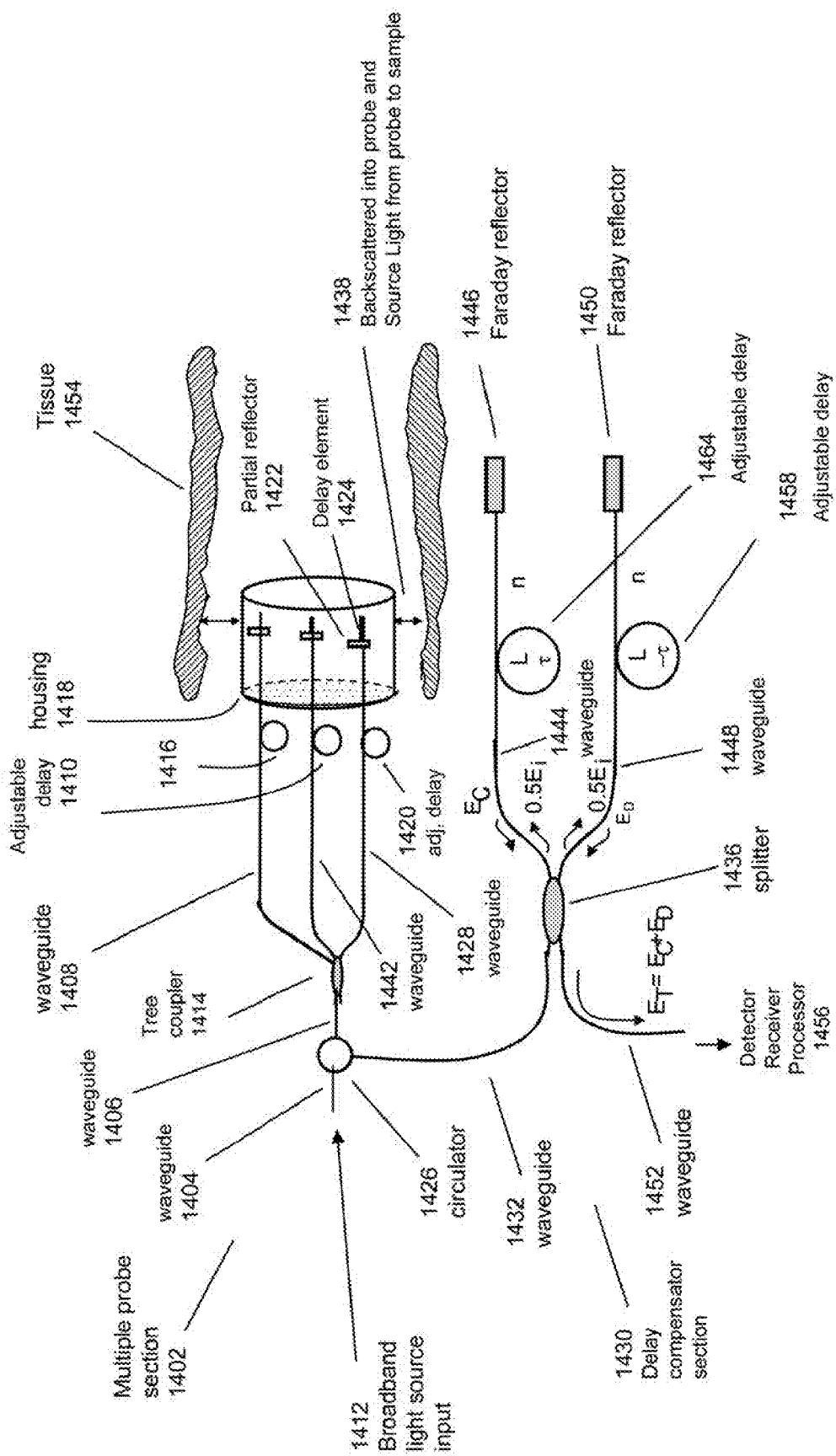

FIG. 14 is an illustration of a version of the present invention capable of being connected or coupled through waveguides to a low coherence light source, a detector and a processor.

Figure 15:
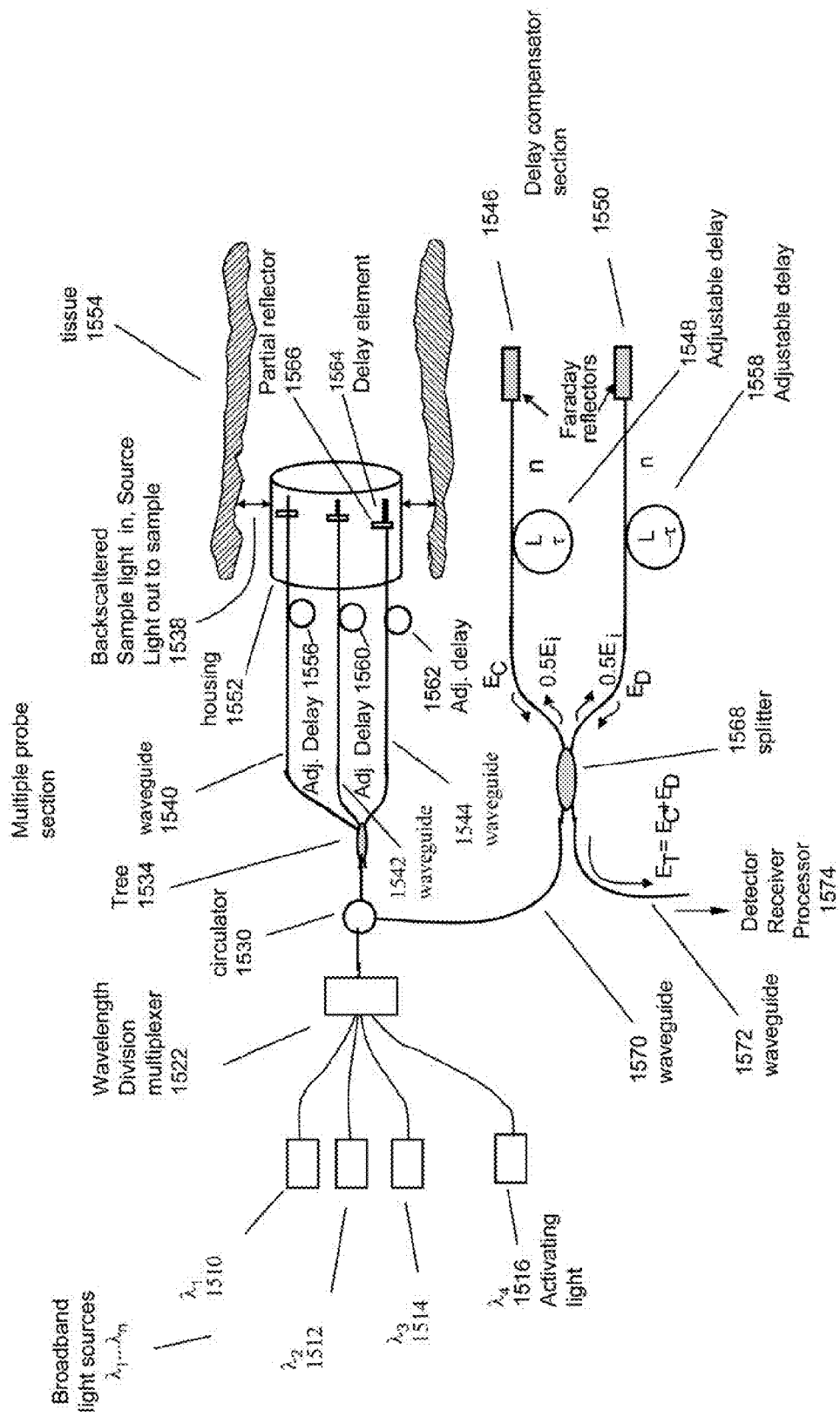

FIG. 15 is an illustration of a version of the invention that may be used to characterize tissue; the device can be coupled through waveguides to multiple wavelength low-coherence sources and coupled to a light source for activating a pharmaceutical agent in contact with the tissue.

Figure 16:
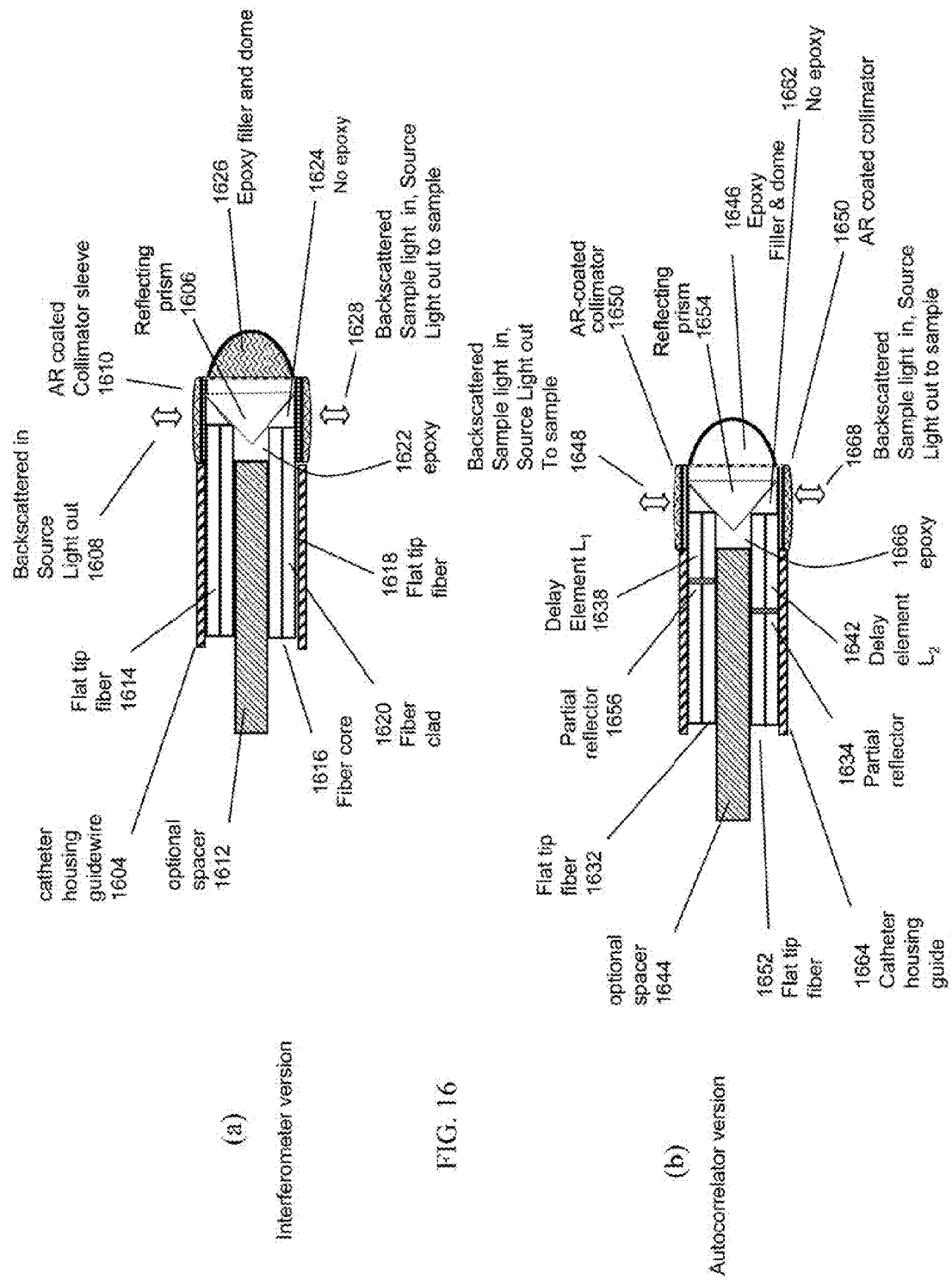

FIG. 16 illustrates versions of the invention having waveguides inside a housing and having a collimator sleeve, or individual collimators, for directing low coherence light to a sample and collecting backscattered light from the sample.

DETAILED DESCRIPTION

Before the present compositions and methods are described, it is to be understood that this invention is not limited to the particular molecules, compositions, methodologies or protocols described, as these may vary. It is also to be understood that the terminology used in the description is for the purpose of describing the particular versions or embodiments only, and is not intended to limit the scope of the present invention which will be limited only by the appended claims.

It must also be noted that as used herein and in the appended claims, the singular forms "a", "an", and "the" include plural reference unless the context clearly dictates otherwise. Thus, for example, reference to a "delay" is a reference to one or more optical delays and equivalents thereof known to those skilled in the art, and so forth. Unless defined otherwise, all technical and scientific terms used herein have the same meanings as commonly understood by one of ordinary skill in the art. Although any methods and materials similar or equivalent to those described herein can be used in the practice or testing of embodiments of the present invention, the preferred methods, devices, and materials are now described. All publications mentioned herein are incorporated by reference. Nothing herein is to be construed as an admission that the invention is not entitled to antedate such disclosure by virtue of prior invention.

"Optional" or "optionally" means that the subsequently described structure, event or circumstance may or may not occur, and that the description includes instances where the event occurs and instances where it does not.

Embodiments of the present invention include devices that can have two or more sample arms and one or more variable delay reference arms, the distal ends of the sample arms collecting source light backscattered from a sample. The backscattered light collected by the distal end of each sample arm is combined with reference light and low coherence interferometric signals for each sample arm produced in a single sweep of a variable delay of the device. The interference signal produced by the interaction of reference light and backscattered light for each sample arm can be measured by a detector. Optionally the one or more sample arms have an adjustable delay. The devices of the present invention may be used to characterize a material based on the interference between reference light and low coherence light backscattered from the sample. These devices eliminate the need for optical switches or rotatable structures to sequentially address independent sample arms and permit the collection of low coherence source light backscattered from several different samples or from several locations on a single sample utilizing a single sweep of one or more adjustable delays. The interference signals from the device provides information on areas or regions of the sample, and can be used to discriminate between health and diseased tissue.

Versions of the invention include sensing devices that are interferometers and or autocorrelators. The interferometers include multiple sensing arms and one or more reference arms, the autocorrelators include multiple probe arms and an interferometer or delay compensator. The devices use one or more broadband light sources and waveguides configured to enable the collection of low-coherence interferometric (LCI) signals from several samples or several locations of a sample, all in a single trace. The interferometers and autocorrelators include two or more waveguides that collect low coherence source light backscattered from a sample. The backscattered light is from the sample is combined with reference light to produce a low-coherence interferometric signal that is detected by a detector. By sweeping a variable delay of the device, for example an optical delay of a reference arm or delay compensator, interferometric signals corresponding to each of the waveguides collecting the backscattered light from the sample are produced. The low coherence interferometric signals from sensor provide information about the morphology, physical nature, composition, and properties of the of the sample it is in proximity with. The sensor may be used to discriminate between finished surfaces and corroded surfaces, healthy and diseased tissue, and can sample the material or tissue in two or more areas. In applications requiring the collection of several LCI traces in a short time, the collection of information from several locations in a single trace considerably reduce the time for data collection.

Reference arms refer to structures that include waveguides, optical fibers, free space structures, or a combination of these along with one or more reflectors that produce reference light from the low coherence source light that is within the coherence length of the light backscattered from the sample. Examples of reference arms include (422) in FIG. 4, (1310) and (1314) in FIG. 13, and can include an arm in the interferometer section of the autocorrelator, for example (746) in FIG. 7. A delay compensator is an interferometer structure that can include waveguides, optical fibers and reflectors that compensate for the separation of the reference and backscattered light from a sample that is outside the coherence length of the source.

Sample arms can be waveguides, optical fibers, free space structures, or a combination of these that propagate low coherence source light to a sample and collect backscattered source light from the sample. Probe arms refer to a type of sample arm where the waveguide reflects a portion of the source light to provide reference light, propagate source light to the sample, and collect backscattered light from the sample. The probe arms propagate both reference and backscattered light. Probe arms include a partial reflector at a short distance from the tip of the probe. The light reflected from the partial mirror is used as the reference light. The value of the reflection coefficient of the partial reflector determines the amount of the reference light and can be less than 100% percent, is preferably from about 30-36% and is most preferably between 32 and 34%. The sensing arm, which collects the backscattered light, for example the interferometric sensor, may contain an optional modulator whose frequency can be detected by the receiver for amplification and processing.

Adjustable or variable delays can be used in the sample arms, probe arms, reference arms, and delay compensator arms to modify the optical path of light propagating in the arms. The delay can be a time delay, a change in the optical pathlength of the arm, or a change in the index of refraction of a portion of the arm.

Low coherent light or activating light in the sensor devices can be propagated in waveguides, optical fibers, wavelength division multiplexers, Faraday rotators, and in free space. Various structures including but not limited to splitters, couplers, and circulators can be used to couple the propagating light into various structures of the sensor device.

A processor can provide an output, for example but not limited to a digital, current, voltage or combination of these, that is proportional to the interference measured and includes phase, amplitude, or a combinations these between the sample and reference light propagated by waveguide elements of the sensor. When multiple wavelength sources are used to probe a sample simultaneously, an array of photodetectors can be used, one for each wavelength, with a light dispersion element to direct the correct wavelength light to the photodetectors. Alternatively, one or more additional delays can be introduced to separate the various LCI's so that a single detector may be used.

Figure 1:
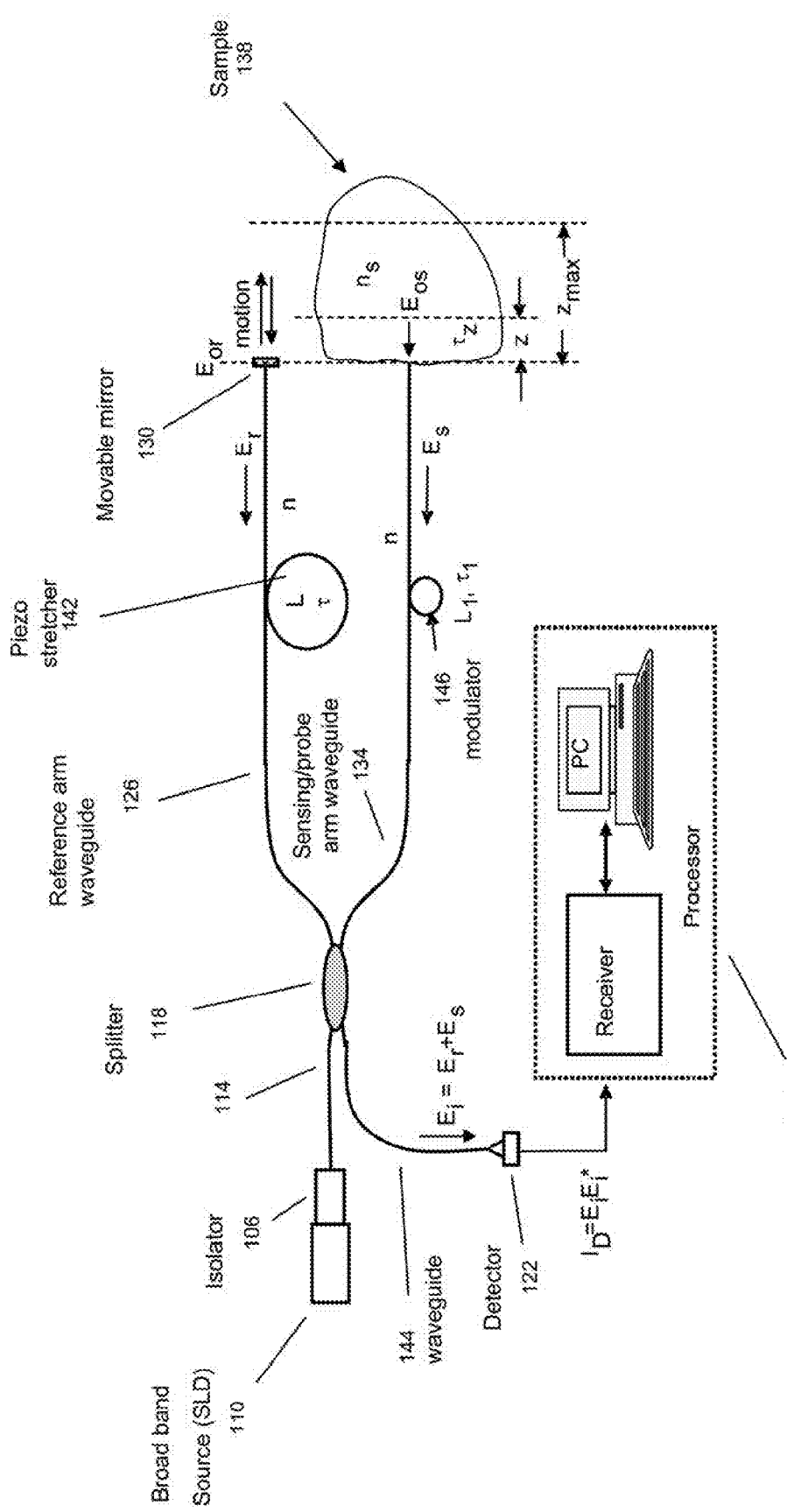
FIG. 1 Is an illustration of an all fiber Michelson LCI interferometer with associated electronics; in the Michelson interferometer, the optical delay in the reference arm can be adjusted by means of the motion of a movable mirror or reflector, or by stretching the length of the arm using a piezoelectric stretcher.

FIG. 1 illustrates the operation of an ordinary single-arm low-coherence Michelson interferometer using single-mode or polarization-maintaining optical fibers. FIG. 1 shows an all-fiber low-coherence interferometer. It consists of a broadband light source (110), such as a superluminescent diode (SLD), an optional isolator (106) coupled to a fiber (114), a fiber splitter (118) (a useful ratio for the splitter is 50:50), an optical detector (122), and two arms: one arm, is referred to as the reference arm (126), that has adjustable length L using piezo stretcher (142) with a mirror (130) at its end and carries the reference light $E_r$; the other arm, is referred to as the sensing arm (134), allows light to penetrate to a distance (z) in a medium, object, or sample (138), and captures the reflected or back-scattered light $E_s$ from the sample (138). The length L in the reference arm corresponds a time delay $\tau$ undergone by $E_r$. Different path lengths for light interacting with the sample may be probed by the interferometric sensor through adjustment of the physical length, optical length, or optical delay of the reference arm of the interferometer. Interference between the reference arm and sample arm light occurs when the optical path length between the two is within the coherence length of the source light. This length or delay can be provided by either moving the mirror (130) at the end of the reference arm, or by providing a device to stretch the fiber. This stretching can be achieved by winding part of the fiber around a piezoelectric (PZT) drum (142) to which a voltage is applied. The PZT stretcher (142) has the advantage of using no mechanical moving parts, and therefore can be relatively fast. By applying a voltage ramp to the PZT (142), the length can be changed or scanned over a given range to provide path length matching with the light from within the sample under study. For scanning over broad ranges, mechanical scan with the moving mirror (130) can be used. For biological tissues, which are highly scattering, the maximum depth $z_{max}$ for penetration of light in the sample is of the order of 1-2 millimeters (mm), and the PZT scan can be used. A 15-meter length of fiber wound around a PZT drum can provide a length, nL, of 5-10 mm, where n is the effective refractive index of the fiber, with the application of a peak voltage of about 500 volts in a 50-millisecond ramp. Several other configurations can be adopted to describe the interferometer. A similar but shorter delay length $L_1$ or time delay $\tau_1$ can be applied to the sensing arm, by the modulator (146).

In operation, light, electric field $E_r$, reflected from the reference mirror (130) and the light, electric field $E_s$, reflected or scattered from depth z within the object or sample (138) under study are combined at the detector (122), whose output current, $I_D$ is proportional to the squared magnitude $E_t E_t^*$ of the total electric field $E_1$, which is the sum of $E_r$ and $E_s$, which is time-averaged and integrated over all frequency components of the light source.

If the power density spectrum of the light source is S(v), then the detector current is given by, (assuming a conversion efficiency of 1 ampere per watt):

$$I_d = \int_0^\infty S(v)(E_r + E_s)(E_r + E_s)^* dv = \quad (1)$$

$$\int_0^\infty S(v)(E_r E_r^* + E_s E_s^*) dv +$$

$$2\text{Re}\left\{\int_0^\infty S(v)E_r(t+\Delta\tau)E_s^*(t) dv\right\}$$

where the star (*) represents the complex conjugate of the total field, and $\Delta\tau$ is the relative time delay between the reference and signal light beams, given by $$\Delta\tau = \frac{nL - nL_1 - n_s z}{c} \quad (2)$$

where n is the fiber refractive index and $n_s$ is the refractive index of the object under test.

If the source spectrum is Gaussian, then $$S(v) = \frac{p}{\sqrt{\pi}} \exp[-p^2(v-v_0)^2], \text{ where } p = \frac{2\sqrt{\ln 2}}{\Delta v} \quad (3)$$

where $v_o$ is the center frequency and $\Delta v$ is the full-width-half-maximum (FWHM) frequency bandwidth of the source. The integrals containing $E_r E_r^*$ and $E_s E_s^*$ yield constant quantities, representing DC currents $I_r$ and $I_s$ from the reference and signal lights alone, and contain no information. The term involving the product $E_r E_s^*$ is the interference signal containing information about the object.

It is convenient to represent the interference signal in terms of the easily measurable center wavelength $\lambda_o$, the FWHM wavelength bandwidth $\Delta\lambda$ of the source, and in terms of the distances L, $L_1$, and z. After some manipulation, the following relationship can be obtained, using $v\lambda=c$, where c is the speed of light in vacuum, and using $\Delta v = c\Delta\lambda/\lambda^2$, $$i_s(z) = 2\text{Re}\left\{\int_0^\infty S(v)E_r(t+\Delta\tau)E_s^*(t) dv\right\} = \quad (4)$$

$$\sqrt{I_r I_s(z)} \exp\left[-\left(\frac{\Delta_1}{L_c}\right)^2\right] \cos\left(\frac{2\pi\Delta_1}{\lambda_o}\right)$$

where $$\Delta_1 = nL - (nL_1 + n_s z), \quad (5)$$

and $$L_c = \frac{2\sqrt{\ln 2}}{\pi} \frac{\lambda_o^2}{\Delta\lambda} \approx 0.44 \frac{\lambda_o^2}{\Delta\lambda}$$

where L is the variable component of the reference arm, $L_1$ is the optional delay added to the sensing arm, and where $L_c$ is the so-called coherence length of the source.

Figure 2:
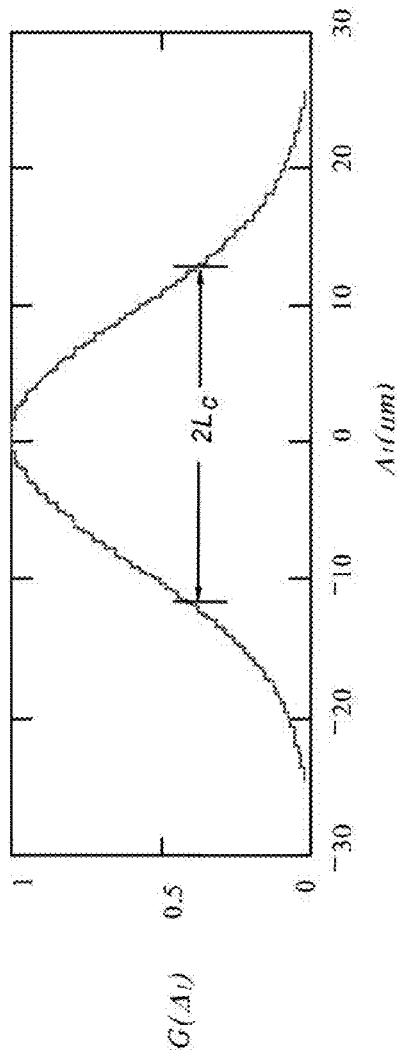
FIG. 2 Is an illustration of the depth dependence of the sensing signal $I_s(z)$ for a skin tissue sample.
Figure 3:
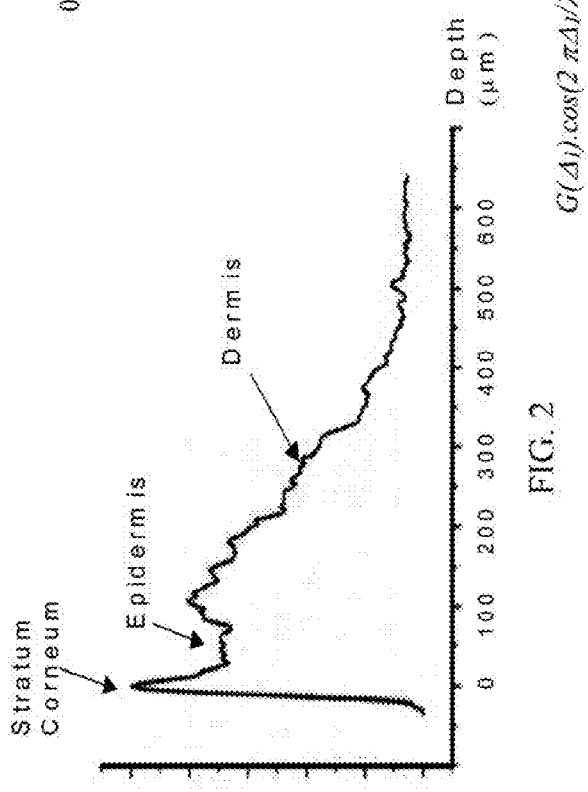

Since $I_r = E_r E_r^* = |E_r|^2$, then $E_r = \sqrt{I_r}$. Similarly, $E_r^* = \sqrt{I_r}$. Moreover, $I_s$ is a function of its starting depth z in the sample and of its reflection and scattering properties. In particular, if the sample is a scattering material, theory shows that $E_s$ has a complicated and exponential dependence on z. This is illustrated in FIG. 2 for a skin sample and $I_s(z)$ can be expressed as a function of z. This type of profile is predicted by scattering theory in general. The specific profile depends on the type of medium, material, or tissue being examined. One of the main features of LCI, as applied to scattering tissues, is to experimentally obtain this profile for arbitrary tissues, whether the tissue is the dermis, as for determining features such as glucose concentration, or arterial walls as for the detection of vulnerable plaques. It is expected that deviations in the composition of a surface, for example due to corrosion, or health of a tissue due to necrosis or presence of a tumor will result in features that are detectable compared to normal surfaces (no corrosion or healthly tissue).

The exponential function in Eq. (4) can be referred to as $G(\Delta_1)$, i.e., $$G(\Delta_1) = \exp\left[-\left(\frac{\Delta_1}{L_c}\right)^2\right] = \exp\left\{-\left[\frac{nL-(nL_1+n_s z)}{L_c}\right]^2\right\} \quad (6)$$

Figure 3:
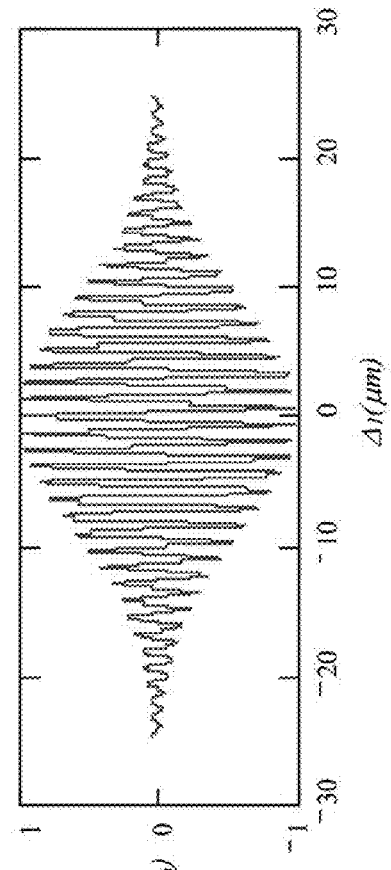
FIG. 3 (*a*) Is a plot of $G(\Delta_1)$ versus $\Delta_1$ illustrating the function of $G(\Delta_1)$ as a coherence gate, (b) is a plot of $G(\Delta_1) \cos(2\pi\Delta_1/\lambda_o)$ versus $\Delta_1$ illustrating an interference signal gated by $G(\Delta_1)$.

In practice L can be made to vary discretely or continuously from 0, even a negative value, or some chosen maximum value and that $\Delta_1$ will vary accordingly. In particular, $\Delta_1$ value is zero when $nL = nL_1 + n_s z$, i.e., when the reference arm length matches the probe arm length for each value of z. The coherence length $L_c$ is a function of the source's center wavelength $\lambda_o$ and FWHM bandwidth $\Delta\lambda$. For example, a source with 1310 nm center wavelength and 50 nm bandwidth, the coherence length is 15 microns. As shown in FIG. 3a, $G(\Delta_1)$ is unity for $\Delta_1=0$; it falls off to 0.37 for $\Delta_1=\pm L_c$, and then rapidly to zero for $\Delta_1 > L_c$.

The cosine term in Eq. (4), $\cos(2\pi\Delta_1/\lambda_o)$, is the real interference, and the argument of the cosine is its phase. It undergoes maxima and minima every time $\Delta_1$ changes by $\lambda_o/2$, with period $\lambda_o$. This is an extremely sensitive function of position and of the refractive index $n_s$ of the sample at position $\zeta$. The product $G(\Delta_1)\cos(2\pi\Delta_1/\lambda_o)$ is plotted in FIG. 3(b). It shows $G(\Delta_1)$ as an envelope which acts as a gate or window which limits the measurable interference signal to a narrow depth of width $2L_c$ and centered at the depth location z which gives $\Delta_1=0$ in the neighborhood of the depth z. Since $I_r$ is a constant and $I_s(z)$ is a function of z, the LCI signal thus is a probing or sampling of the magnitude of the light reflected or scattered from depth z within a resolution of $\pm L_c$.

For a given depth z for which $\Delta_1$ is zero, the interferometric signal is given by its peak value which, from equation (4) is $$i_s(z) = \sqrt{I_r I_s(z)} \quad (7)$$

Thus by ramping L, for example at a constant rate v such that L=vt, where t is the time, and continuously measuring the peak of the detected signal, then the plot of Equation (7) vs. L can be used to plot $I_s(z)$ in a manner similar to FIG. 2 for the sample under test over the full measurable depth $z_{max}$. This can be computed by the processor section (150) illustrated in FIG. 1 connected to the detector.

In a typical LCI or OCT (optical coherence tomography) system, only the magnitude of the interference is measured, and the process is essentially as described above. More sophisticated systems can be designed to measure both the magnitude and the phase of the signal interference signal. Such systems are described in detail in Patent Applications invented by Gerard A. Alphonse and assigned to Medeikon Corporation Exp. Mail No. EL 732725416 US, titled LOW COHERENCE INTERFEROMETRY UTILIZING MAGNITUDE, and Exp. Mail No. EL 732725393 US, titled LOW COHERENCE INTERFEROMETRY UTILIZING PHASE the contents of each being incorporated by reference in the present application in their entirety. Although the remainder of the present application will be described with reference to amplitude measurements of interference, the claims are not limited to amplitude measurements of interference and may include phase measurements and combinations of these where applicable.

The sensors in various embodiments of the present invention are devices that can have two or more sensing arms and one or more reference arms. The plurality of sensing arms in an interferometer or plurality of combined reference and sensing arms in an autocorrelator can be configured to acquire low coherence interferometric information on a sample(s) from all the arms in a single trace during a sweep of a variable delay of one or more reference arms or a delay compensator. Through use of appropriate delays in the sample arms, for example a time delay, refractive index change, a change in length of a waveguide, or any combination of these in any of the sample arms, the individual low coherence interferometric signals from each of the sample arms may be resolved or separated.

In many sensing and diagnostic applications the collection of several LCI signals in a short time either from a single sample region or from several regions or directions along a sample is beneficial in terms of reduced examination time and reduced costs. Further, the configuration of the sample arms and reference arms in the present invention eliminates the complexity and costs associated with use of an external optical switches or multiple interferometers, even those formed on a single substrate, to simultaneously probe different areas of a sample.

The optical sensor device in embodiments of the present invention may consist of elements from a free space device, fiber optic elements, integrated optics, or a combination of these. While free space device configurations are possible, waveguides, such as but not limited to monolithically formed channel guides or optical fibers are preferred in the present invention. Through the use of multiple waveguides for sample arms to propagate low-coherence light and to collect backscattered light from the sample, information about the sample may be obtained in a single sweep of the variable delay of a reference arm or delay compensator. This obviates the need and limitations of birefringent crystals or optical switches to address multiple sample arms. The use of waveguides provides greater latitude in the size, shape, and flexibility in the design and use of borescopes, endoscopes, and catheters for probing a wide variety of cavities, vasculatures, and conduits.

Light sources useful in the present invention can include those which are capable of penetrating material samples and providing torturous as well as ballistic light trajectories in the sample. Examples of such light sources include low coherence light sources or multiple low coherence light sources with different center wavelengths whose outputs have been combined. The source may emit in the near infrared and infrared, have a short coherence length, and have high irradiance for penetrating deep into the sample. Preferably for probing tissue, the low coherence light sources have wavelengths in a range of from about 600 to about 1800 nm. Examples of sources include but are not limited to edge emitting LEDs, superluminescent diodes, and multiple quantum well light emitting diodes. One or more light sources having the same or a different wavelength may be used or one or more multiple quantum well devices may be formed on a single substrate to provide multiple wavelengths. The penetration of light into a material sample, preferably a tissue sample can vary with the wavelength and power of the of source light used, use of optical circulators, coupling losses and component attenuation of light, and the type of material being scanned. As an illustrative example for the sensor depicted in FIG. 15, low coherence light sources (1510), (1512), (1514) and others (not shown) each having a different center wavelengths can be coupled before the circulator (1530) through a wavelength division multiplexer (1522) (WDM). In use the sample (1554) may be illuminated by a low coherence light source with a center wavelength of for example 800 nm, 1300 nm, or 1800 nm. By using more than one wavelength of low coherence source light to probe the sample, the sample can be probed at different depths and spectroscopic information about the sample can be obtained during a trace.

The profile of the light beam profile outside of a waveguide or fiber can be modified to maximize backscattered light collected by the waveguide. Collimating the beam can be used to achieve this for example by use of a GRIN lens, the use separate microlens fixed to the end of the waveguide or fiber, a collimating structure fabricated on the outside of the glass wall such as those as illustrated by structures (1610) and (1650) in FIG. 16, or laser micromaching the tip of the fiber. FIG. 16(a) illustrates a probe for an interferometer that has a housing (1604) enclosing two or more sample arms (1614), (1618), and others not shown. The sample arm waveguides (1614) and (1618) propagate light to the reflecting prism (1606) where it is directed radially out through a collimator sleeve (1610) mounted to the housing (1604). Source light and backscattered light (1608) from a sample that is propagated by waveguide (1614) passes through the collimator (1610) while source light and backscattered light (1628) from a sample that is propagated by waveguide (1618) also passes through the collimator (1610). FIG. 16(b) illustrates a probe arm that has a housing (1664) and waveguides (1632) and (1652) each having partial reflectors (1656) and (1634) respectively and delay elements (1638) and (1642) respectively. Source light and backscattered light (1648) from a sample that is propagated by waveguide (1632) passes through the collimator (1650) and source light and backscattered light (1668) from a sample that is propagated by waveguide (1652) passes through the collimator (1650). An optional spacer (1612) or (1644) may be included in the housing to maintain the spacing of the fibers within the housing.

FIG. 4 shows an embodiment of multiple probes based on a Michelson interferometer having multiple sensor arms (410) and (414) and others (418) and a single reference arm (422). In this configuration, the single sensing arm of the standard interferometer is replaced by a multiplicity of sensing arms joined together by means of a 1:N coupler (426) such as a commercially available star or tree coupler. This tree coupler (426) preferably splits its input light equally among the N branches. The preferred splitting ratio at the main splitter (430) dividing light between the reference and sample sections is about 50:50 (50% for the reference arm and 50% for the tree coupler).

In FIG. 4, the different branches are shown to probe the same general area of a sample (438). Without limitation the sample arm branches can be oriented in different directions on the sample, the branches may be in contact with different samples, or the branches may be in contact with a sample and a reference material. The operation of the system can be analyzed in the same manner as the ordinary interferometer, with the input electric field to the detector being the sum of the electric fields returning from the reference arm (422) and all the sensing arms (410), (414), and others (418). The analysis of the interferometer, vide infra, is shown for two sensing arms, but the results can be extended to an arbitrary number of sensing arms. In the case of two sensing arms (410) and (414), the total electric field $E_i$ at the detector (442) is the sum of the reference field $E_r$ and those of the two sensing arms $E_{s1}$ and $E_{s2}$. The resulting detector current may be given by Eq. 8:

$$I_d = \int_0^\infty S(v)(E_r + E_{s1} + E_{s2})(E_r + E_{s1} + E_{s2})^* \, dv \quad (8)$$

from which the interferometric signal is found to be a single trace having the two components $$i_s(z) = i_{s1}(z) + i_{s2}(z) = \sqrt{I_r I_{s1}(z)} \exp\left[-\left(\frac{\Delta_1}{L_c}\right)^2\right]\cos\left(\frac{2\pi\Delta_1}{\lambda_o}\right) + \sqrt{I_r I_{s2}(z)} \exp\left[-\left(\frac{\Delta_2}{L_c}\right)^2\right]\cos\left(\frac{2\pi\Delta_2}{\lambda_o}\right) \quad (9)$$

where $$\Delta_1 = nL - (nL_1 + n_s z), \quad (10)$$
and
$$\Delta_2 = nL - (nL_2 + n_s z)$$

An important aspect of this invention is the ability to independently retrieve these two components, in other words to completely or partially prevent them from overlapping in the LCI trace. The key lies in the choice of the total scanning distance L, of the reference arm (422), the individual sensing arm distances $L_1$ and $L_2$, and the gating property of the functions $G(\Delta_1)$ and $G(\Delta_2)$ shown below $$G(\Delta_1) = \exp\left[-\left(\frac{\Delta_1}{L_c}\right)^2\right] \quad (11)$$
and
$$G(\Delta_2) = \exp\left[-\left(\frac{\Delta_2}{L_c}\right)^2\right]$$

FIG. 5 illustrates how two LCI profiles from separate sample arms can be resolved with a single trace of the reference arm (422). This can be achieved, for example, by allowing the instrument shown in FIG. 4 to scan the reference arm (422) length L at speed v over a time duration t, with the sample arms configured so that $L_2 > L_1 + z_{max}$ and $L > L_2 + z_{max}$. In this configuration independent observe or measure the back-scattered LCI profiles $I_{s1}(z)$ and $I_{s2}(z)$ can be made. FIG. 5 shows the appropriate relationship among $L_1$, $L_2$, $z_{max}$, and L to achieve complete resolution of profiles $I_{s1}(z)$ and $I_{s2}(z)$. If $L_2 = L_1$, then the two signals will occupy the same space in the trace. However, if $L_2 > L_1 + z_{max}$, then $I_{s2}(z)$ will be separated from $I_{s1}(z)$ by a distance equal to $n_2 L_2 - n_1 L_1$ where $n_2$ and $n_1$ are the refractive indices of the sample arms. When $L > L_2 + z_{max}$, then both LCIs will be fully separated and complete, as illustrated in FIG. 5. The configuration and assembly of a sensor with more than two probes where the low coherence interferometric signals from at least two of the sample arms is partially resolved, preferably where the low coherence interferometric signals from all of the sample arms are completely resolved, can be made using these criteria.

In various configuration of the devices in the invention, for example those utilizing two or more sample arms coupled to one or more reference arms, or two or more probe arms coupled to a delay compensator, it is possible to use materials with different indices of refraction, mirrors, or fiber stretching to modify an adjustable delay resulting in partial or complete resolution of the individual LCI signals from the backscattered sample light collected by the sample arms. Complete LCI signal resolution may be achieved, partial resolution of LCI signals from one or more of the sensing arms may be achieved, or a combination of these may be achieved. Resolution refers to the process or capability of making distinguishable at least some of the individual parts of the interference signal from two or more sample or probe arms produced during a single sweep of the adjustable delay of the reference section or delay compensator respectively. Where partial resolution is achieved, adjustments, including but not limited to the size of L, $L_m$, (where m is an integer describing the number of sample or probe arms in the sensor), the index of refraction n of the sample, probe delay adjustment, delay compensator arms adjustment, adjustment of one or more reference arm(s), or adjustment of the depth of penetration of light in the sample z can be used to modify the degree of separation achieved between multiple LCI signals.

One version of the invention is an interferometric sensor including two or more sensing arms each having an adjustable delay (416) and (420), and a reference arm also having an adjustable delay (412) as shown in FIG. 4. The sensing arms and reference arms can be coupled (430) to one or more low coherence light sources (404) and utilize an optional isolator (408). The reference and sample arms of the sensor may be configured, for example by a change in their length, a delay time, position of moveable mirror (434), or a change in the index of refraction of the guide so that the delay for each of the sample arms and reference arm is within the coherence length of the source light. Backscattered sample light from the two or more sensing arms and the reference arm light are coupled together and interference measured by detector (442). A signal proportional to the interference measured for each of the sample arms during a sweep of the delay (412) can be displayed, compared to normal material, or digitized using processor (450).

Various devices of the present invention may include light sources, detectors, and processor, or components of these devices may be connected to pre-existing light sources, detectors and other components using waveguides and electrical connectors. For example, the interferometric sensor of FIG. 4 may include a low-coherence light source. Alternatively, splitter (430) can be coupled to one or more pre-existing low-coherence light sources available in a hospital or laboratory. The interferometric sensor described can be coupled to a separate or existing detector using waveguide (446), or it may include a dedicated detector (442) to measure the intensity of interference between the reference and light backscattered from the sample. The detector may further be connected to an existing processor, or a dedicated processor (450) as shown in FIG. 4, that can provide an output, for example but not limited to a digital output, a current output, or a voltage output that is proportional to the interference between the backscattered light and reference arm (or delay compensator adjusted) light measured by the detector for each sensing arm. Preferably adjustment of the reference arm adjustable delay or the delay compensator adjustable delay is capable of resolving backscattered light information from at least two sample or probe arms. The adjustable delay in the delay compensator arms, reference arms, or sample arms can be voltage actuated, current actuated, digitally actuated, or actuated by a combination of these. The sensor devices preferably includes sample, delay compensator, and reference arms which are made from fiber or single-mode waveguides and preferable uses polarization-maintaining waveguides.

LCI autocorrelators can also be configured to have multiple sample or probe arms. One of the advantages of the autocorrelator is that they can be built from single-mode fibers, which is less expensive and less complicated to use than polarization-maintaining fibers. FIG. 6 shows an example of an autocorrelator. It consists of an interferometer and an independent probe (610) which carries both the reference light and the sensing light. A portion of the source light (618) is partially reflected light from the partial reflector (614) near the tip of the probe (610) to form reference light $E_r$. The sensing light is the light transmitted into the sample (638) and back-scattered and propagated by fiber (610). Thus, there is a distinct delay between the reference and sensing light, the delay being twice the distance the light travels beyond the fiber tip and into the sample. This distance is much longer than the coherence length of the source (618), and therefore the reference and object light cannot interfere with each other. The path length correction for interference can be provided by the interferometer. The probe (610) is connected to the broadband source (618) (the isolator (620) is optional) by means of a circulator (622). A circulator (622) is a three-port device in which light injected at one port is transmitted to a second port, but the light reflected from the second port is deflected to a third port; a splitter can also be used, but the isolator is more efficient. The electric field of the reference light can be designated as $E_r$, starting from the value $E_{or}$ at the reflector. The field from the sensing light may be designated as $E_s$, and its initial value is $E_{os}$. A short length $L_1$ of fiber (624), terminated preferably with an antireflection coating, can be used to provide a controlled delay $\tau_1$.

An advantage of having the reference and sensing lights in the same fiber when using single-mode fiber is the fact that the relative polarization between the two lights is maintained under any circumstance. This is important because interference occurs between the light beams when they have the same polarization. In the event the extra waveguide length $L_1$ is used, it is preferable for it to be a section of polarization-maintaining fiber, or any material that minimizes loss of polarization, in order to avoid any loss of polarization in short length $L_1$ of fiber (624). This arrangement is easily achieved, for example but not limited to deposition of a partial mirror at the end of the main fiber (614), then fusion of the element with delay $L_1$ (624) piece to the partial mirror.

The total electric field in the probe, which is the sum of $E_r$ and $E_s$ is directed to the interferometer from the third port (628) of the circulator (622). This light serves as the input to the interferometer or delay compensator section of the device.

The delay compensator consists of two similar arms (632) and (634) that can be made to have identical or nearly identical lengths or delays with two devices (642) and (646), that can be but are not limited to a PZT fiber stretcher. The devices (642) and (646) are also capable of providing a variable relative delay between the delay compensator arms (632) and (634). The delay can be obtained by a mechanical device, for example a voltage, current, or digitally actuated moving reflector. A preferred device can include winding a length of the fiber (632) and (634) in each arm around separate PZT drums and applying a voltage to the PZT drums. The application of a voltage of one polarity expands the PZT drum, hence stresses the fiber to increase its length by the amount L and provide a delay $\tau$. Applying a voltage of the reverse polarity will have the opposite effect. By applying a voltage of one polarity to one drum (642) and of the opposite polarity to the other drum (646), a round trip effective path difference of 4L or a delay of 4$\tau$ can be achieved. As an example, a 15-meter length of fiber wound around a PZT drum can provide a length nL of 5-10 mm, with the application of a peak voltage of about 500 volts in a 50-millisecond ramp. To preserve the polarization relationship of light in the two reference arms (632) and (634), especially upon reflection, Faraday rotator reflectors (650) and (654) can be used in the interferometer.

In operation, the delay compensator input light $E_i=E_r+E_s$ is coupled to the delay compensator and is split by the splitter (658) into two equal components which, upon reflection from the Faraday mirrors (650) and (654), becomes $E_C$ and $E_D$, with their respective delays, so that the total light input to the detector is $E_T=E_C+E_D$. The mathematical analysis of this system shows DC terms, some interferometric terms with delays that are always much larger than $L_c$ (the coherence length) and therefore are vanishing, and two terms which combine to give the current $i_s(z)$ $$i_s(z) = (1-R)\sqrt{R}\sqrt{I_r I_s(z)} \exp\left[-\left(\frac{\Delta}{L_c}\right)^2\right]\cos\left(\frac{2\pi\Delta}{\lambda_o}\right) \quad (12)$$

where R is the power reflection coefficient at the probe tip, and where $$\Delta = 4nL - 2(nL_1 + n_s z) \quad (13)$$

By applying a voltage of one polarity to one drum (642) and of the opposite polarity to the other drum (646), a round trip effective path difference of 4L or a delay of 4$\tau$ can be achieved. Without limitation, other path length differences may be achieved in the delay compensator by applying different voltages to the drums so that the difference in Eq. 13 is within the coherence length of the source light and interference occurs.

This result is similar to the ordinary Michelson interferometer except for the fact that Δ is double the difference between the scan length and the path length between the reference and sensing lights. The common path between the reference and signal cancels out. Thus, although the path difference between the reference and sensing lights in the probe arm (610) is much larger than the coherence length, the delay compensator path difference can bring it under the coherence gating function. In particular, the detector (662) can measure the peak of the signal corresponding to any depth z with the sample is obtained when $2nL=nL_1+n_s z$.

One version of the invention is a sensor that includes two or more probe arms that are capable injecting source light into a sample and collecting backscattered light from the sample and capable or producing reference light. The probe arms are coupled to a tree splitter which is itself coupled to a low-coherence light source through a circulator or splitter. Each probe is configured so that it propagates reference light and also propagates light backscattered from the sample. This is done by inserting a partial reflector at a short distance from the tip of the probe. The light reflected from the partial mirror can be used as the reference light. The value of the reflection coefficient of the partial reflector determines the amount of the reference light. The light that is transmitted through the section of the waveguide beyond the partial reflector is used as the probing light itself, and this section of waveguide is used to transmit the probe light to the sample and collect the backscattered light from it. This backscattered light is then coupled to the main section of the probe through the partial reflector. In this manner, the probe contains both the reference light and the backscattered light. The short distance between the partial reflector and the tip of the waveguide provides a well defined delay between the reference light and the backscattered light. In a multiple probe arm instrument, each arm would have an appropriate length determined by the amount of separation desired among the signals from the individual arms, and the various arms are joined together using a tree coupler. The 1×N tree coupler is an optical component that enables light to be coupled from one waveguide to N waveguides and vice-versa. In various versions of the invention, the tree coupler is used to split the light from a broadband light source equally among the N branches. In the case of a device using probe arms, the tree coupler splits light from the broadband source among the N branches and then combine the light backscattered from the sample (the reference lights and the backscattered lights) back into that single waveguide. Light from a broadband source can be coupled to the multiple-arm probe by using another coupler, which is preferably a circulator. The circulator prevents the reflected light from affecting the broadband light source. In this version of the invention, the sensor also includes a delay compensator or delay equalizer, which is connected to the third port of the circulator such that the total reflected light in the multiple-probe arms from the sample is fed to the delay compensator. The delay compensator is an interferometer which consists of two delay arms with adjustable delays between them, and reflectors at the end of each arm. In order to maintain polarization, particularly if the delay arms are made from single-mode fibers (as opposed to polarization-maintaining fibers), Faraday rotator reflectors are used. A Faraday reflector consists of a Faraday rotator and a mirror. The light entering a fiber from a Faraday reflector is such that its polarization is exactly the same as that of the light entering the Faraday reflector from the fiber. The purpose of the adjustable delays is to compensate for the fact that the respective delay between the reference and backscattered light in any individual probe arms is normally significantly larger than the coherence length, and therefore cannot interfere together by themselves. The compensator delay compensates for that delay and brings the interference between these two lights to within the coherence length of the light source by compensating for the original delay between them.

The adjustable delay can be obtained in several ways. One way is to make the position of the mirror of the Faraday rotators individually variable. Another way is to make the length of the two arms of equal or different lengths and including a fiber stretcher in each arm for providing the delay or for fine-tuning of the delay. The delay arms of the interferometer component connected to the third port of the circulator are configured such that all the interferences between the reference and backscattered light from all the probes occurs sequentially under a single trace of the delay compensator arms through their adjustable delay. The various interference signals appear within the gating windows determined by the coherence length of the light source. The interference signals are measured by a detector that can be coupled to one of the return leads of the splitter in the interferometer section.

The sensor devices can include one or more a low-coherence light source including an activation light source for photodynamic therapy, or subcomponents of the sensor device, for example it may be connected to an existing low-coherence light source. A detector, which may be a separate existing detector or a dedicated detector, can be coupled to the circulator, and the delay compensator arms. The detector measures the interference between the light reflected from the partial reflectors and backscattered light from the sample that is collected by the individual probe arms. The detector may further be connected to a processor that provides an output proportional to the interference signals. In this version of the sensor, the probe is preferably configured so that interference between reflected source light and backscattered source light from the sample does not occur directly, but rather as a result of the compensation delay in the interferometer or delay compensator section. Preferably the polarization of light in both the probe and delay arms is maintained, even more preferably Faraday mirrors are used as reflectors in the delay compensator arms, interferometric arms, of the sensor. The adjustable delay in the probes or delay arms may be electrically or digitally actuated to achieve the desired delay between the interferometer arms, length matching or modulation of the reference section of the probe arms. Where the length of the probe arms are adjusted, preferably the length of waveguide between the sample and the partial reflector is not equal for two or more probes.

An autocorrelator with multiple probes is shown in FIG. 7. Instead of the single probe of the ordinary autocorrelator illustrated in FIG. 6, the autocorrelator now has a multiple probe branches or sample arms (708), (710), and other probe branches or sample arms (712) coupled to a star or tree coupler (704) that is itself coupled, or capable of being coupled, to a circulator (722) with output ports (706) and (728). Each probe branch consists of a common path waveguide for the reference and backscattered sample light, the waveguide may be an optical fiber or a monolithically formed waveguide on a substrate. Light from one or more low coherence sources (718) through optional isolator (720) is propagated to the sample (738) through port (706) of the circulator (722), through tree coupler (704) coupled to the multiple probe arms (708), (710), and other probe arms (712). The waveguide for each probe branch has a partial reflector near the end of the waveguide, such as (714), (716), and partial reflectors not show for the other branches (712), and a unique delay element, such as ((724) with delay $L_1, \tau_1$)) and ((726) with delay $L_2, \tau_2$), and delay elements not shown for the other branches with delays $L_m$, $\tau_m$) where m is an integer representing the other branches present. The length of the delay elements are chosen so that the path difference between the reference light and sensing light is larger than the coherence length of the source. The delay elements may be fused to the partial mirror deposited on the end of the waveguide or fiber. The delays would be located after the partial reflector along the waveguide. The delay elements, such as (724) and (726), can be designated by the lengths $L_1$, $L_2$, up to $L_m$, or the time delays $t_1$, $t_2$, up to $t_m$. Optionally, it is also possible to add to each arm the small delays such as length adjust elements, (730) and (734), which can be small PZT drums on which are wound the small fiber sections to provide the length-adjust elements $\delta_1, \delta_2, \ldots \delta_m$ and $d_1, d_2, \ldots d_m$.

FIG. 7 also illustrates the three sections for an autocorrelator version of the present invention that includes a probe section (702), delay compensator section (740), and signal processing section (760). The multiple probes (708), (710), and (712) carry both reference and backscattering signals and along with the optional adjustable delay(s) ((730), $\delta_1$ and $d_1$) and (734), $\delta_2$ and $d_2$) that make up the probe section. The delay compensator section includes the waveguides (742) and (746) with variable delays ((744), L and $\tau$) and ((748), L and $-\tau$) and Faraday reflectors (750) and (754) and is used to compensate for or equalize the path differences between the reference and backscattered lights in the individual probe branches. The detector or signal processing section (760) includes the detector (766) and processor (768) that are coupled or capable of being coupled by waveguides (770) and (774) to the circulator (722) and interferometer delay compensator section through splitter (758).

The electric field in each branch of the multiprobe is the sum $E_{rk}+E_{sk}$ of the reference field $E_{rk}$ and signal field $E_{sk}$ in that branch, where k is an integer (k=1, 2, 3, ... up to number of probes). These fields are summed together in the tree coupler (704) and fed to the interferometer or delay compensator through the output port (728) of the circulator (722). All the electric field elements will interact and interfere at the detector (766) after passage through the interferometer, but that only those interactions which, together with the interferometer delay, can exhibit a path difference shorter than the coherence length will produce a useful LCI signal. In particular, it is expected that the field from each signal branch can interfere not only with its own reference field (self-referenced), but also with the reference fields from all the other branches to produce additional LCI signals for that particular branch (cross-referenced). The presence of crossed-referenced signal components can be used to provide automatic averaging or summing of an LCI without the need for repeated scanning.

The multiple combined reference and sensing probe arms of an autocorrelator can be used to produce LCI signals from all the sample arms during a single sweep of one or more variable delays of the delay compensator. The probe arm also has a variable delay, for example variable length $L_m$ or time $\tau_m$. By applying appropriate delays to the delay compensator, it is possible to produce LCI signals for each of the probe arms by virtue of the gating property of the exponential function $G(\Delta)$.

For an autocorrelator having multiple probe branches or sample arm, the total backscattered interferometric signal may be described by the backscattered light propagated by each of the branches as well as cross terms related to the combination of the reference light from the branches. For two probe branches, the LCI signal can be described by the following expression containing the following four terms:

$$i_s(z) = i_{s11}(z) + i_{s12}(z) + i_{s21}(z) + i_{s22}(z) \quad (14)$$

where assuming, for simplicity, that the power reflection coefficient for the reference light at each branch has the same value R:

$$i_{s11}(z) = (1-R)\sqrt{R}\sqrt{I_{r1}I_{s1}(z)} \exp\left[-\left(\frac{\Delta_{11}}{L_c}\right)^2\right] \cos\left(\frac{2\pi\Delta_{11}}{\lambda_o}\right), \quad (15)$$

where
$$\Delta_{11} = 4nL - 2(nL_1 + n_s z)$$

$$i_{s12}(z) = (1-R)\sqrt{R}\sqrt{I_{r2}I_{s1}(z)} \exp\left[-\left(\frac{\Delta_{12}}{L_c}\right)^2\right] \cos\left(\frac{2\pi\Delta_{12}}{\lambda_o}\right), \quad (16)$$

where
$$\Delta_{12} = 4n(L + d_1 - d_2) - 2(nL_1 + n_s z)$$

$$i_{s21}(z) = (1-R)\sqrt{R}\sqrt{I_{r1}I_{s2}(z)} \exp\left[-\left(\frac{\Delta_{21}}{L_c}\right)^2\right] \cos\left(\frac{2\pi\Delta_{21}}{\lambda_o}\right), \quad (17)$$

where
$$\Delta_{21} = 4n(L + d_1 - d_2) - 2(nL_2 + n_s z)$$

$$i_{s22}(z) = (1-R)\sqrt{R}\sqrt{I_{r2}I_{s2}(z)} \exp\left[-\left(\frac{\Delta_{22}}{L_c}\right)^2\right] \cos\left(\frac{2\pi\Delta_{22}}{\lambda_o}\right), \quad (18)$$

where
$$\Delta_{22} = 4nL - 2(nL_2 + n_s z)$$

The star or tree coupler, for example (704) in FIG. 7, can be made so that $I_{r1}=I_{r2}$. Comparing Equations 15 and 16, it is apparent that $i_{s11}(z)$ and $i_{s12}(z)$ are both LCI signals for $I_{s1}(z)$, and that they are exactly equal if $d_1=d_2$. In other words, when $d_1=d_2$, not only do $i_{s11}(z)$ and $i_{s12}(z)$ have the same magnitude, but also they occupy the same position in space or time within the overall trace, and therefore they add up. Similarly, from Equations 17 and 18, the same is true for $i_{s21}(z)$ and $i_{s22}(z)$ as being LCI signals for $I_{s2}(z)$. Therefore, when $d_1=d_2$, the LCIs for $I_{s1}(z)$ and $I_{s2}(z)$ are the sums given below $$i_{s1}(z)=i_{s11}(z)+i_{s12}(z)=2i_{s11}(z) \text{ and } i_{s2}(z)=i_{s21}(z)+i_{s22}(z) = 2i_{s22}(z) \quad (19)$$

Practically the length of the probe branches (708), (710) and (712) can be made to be as similar as possible. The length adjust elements (730) and (734) that provide the delays $d_1$ and $d_2$ and others not shown can also be used with appropriate voltages applied to the PZT drums to change or equalize the probe branch lengths.

Speckle noise causes random variations in LCI signals. In ordinary interferometers or autocorrelators, the speckle can be averaged out by repeating the LCI measurements for a given sample arm and adding up the individual LCI's in time. This signal addition or averaging process is automatic and at the cost of no extra sampling or processing time in the multiprobe system in versions of the present invention. This is advantageous and can be applied to a system having any number of probe branches. For a 1:N star coupler, the light in each branch is reduced by a factor of N, but that reduction factor is offset by the fact that each LCI is increased and averaged by the same factor.

A further randomizing to reduce the speckle noise can be obtained by not making $d_1$-$d_2$ exactly zero, but rather by providing or maintaining a small randomized difference (wiggle) between $d_1$ and $d_2$. This can be done by applying a small modulation (with amplitude of the order of one or more optical wavelengths, i.e., a few microns) on either $d_1$, $d_2$, or both. The modulation to (730) and (734) may be electrically or digitally controlled. The frequencies of the wiggles can be the same for all the branches or can be slightly different for each, but with random starting phase. The frequency is preferably higher than the scan rate of the interferometer. For example, for a scan time of 50 milliseconds, it is sufficient for the wiggling frequency to by higher than 20 Hz. From Equations 16 and 17, a non-zero value of $d_1$-$d_2$ makes $\Delta_{12}$ to be slightly different from $\Delta_{11}$ and causes the exponentials to peak at slightly different locations. Thus, a slight modulation of $d_1$-$d_2$ causes $i_{s12}(z)$ to wiggle around a fixed $i_{s11}(z)$ and similarly $i_{s21}(z)$ to wiggle around a fixed $i_{s22}(z)$. This can accomplished by applying small radio frequency voltages to the individual PZT elements to change the individual lengths by a value of the order of $\lambda_o$. Since the LCI signal is peak-detected, the phase information is lost by the wiggling process and so the speckle noise is averaged out. This capability for "wiggling" the cross-referenced components of an LCI signal provides a way to reduce noise in an autocorrelator sensor and can also be applied to an interferometer having multiple reference arms as illustrated in FIG. 13. Just as for the multiprobe interferometer, $i_{s1}(z)$ and $i_{s2}(z)$ are fully separated in the two-branch autocorrelator system if $L_2 > L_1 + z_{max}$.

The multiprobe autocorrelator and interferometric sensors may be used to measure and characterize a variety of materials and structures where flexible fiber scopes cannot be articulated to view nearby or lateral surfaces. In addition, where there is limited time for scanning or large surface areas to be scanned, it can be advantageous to use multiple probes or waveguides and acquire LCI information from a plurality of probes in a single scan. The detection of plaque in human arteries is a non-limiting example of an application where narrow passages preclude articulation of a probe to face the walls of the artery and where there can be a large area that needs to be scanned with a technique having micron or submicron resolution. Although reference will be made to the configuration and use of versions of the present invention for characterizing arteries, other configurations and uses of the sensors are possible.

FIG. 8(a) illustrates an implementation of the use of the multi-branch probe sensor to a catheter to be used in an LCI interferometer or autocorrelator which could be used for the detection of vulnerable plaques inside human arteries. Without limitation the same or a similar multi-branch probe sensor could be used in a borescope, an endoscope, laparoscope, or other inspection device. The inspection device may be rigid or it may be flexible and is preferably made from chemically compatible and if required a bio-compatible material that is suitable surface finish for contact with a material or tissue to be examined. Examples of housing materials include but are not limited surgical steels, titanium alloys, as well as transparent perfluorinated polymers like MFA and FEP and combinations of these.

As illustrated in FIG. 8(a), the various sample branches of an interferometer sensor, for example waveguides (818), (822), and (826), (additional waveguide branches (820), (824), (828), are illustrated in FIG. 8(b)) are brought together and placed inside a housing (858) covering a portion of two or more light propagating probe branches, the probes capable of guiding light from a low coherence source, coupled to waveguide (810) through a splitter or circulator (not shown), to a sample and guiding backscattered light from the sample to a reference section through a circulator or splitter (not shown) coupled to waveguide (810). Each probe can have an optional adjustable delay, for example (830), (834), and (838) that can be used with a variable delay in one or more reference arms of the reference section to provide resolution of two or more low coherence interferometric signals from the sample arms (818), (822), and (826) with a single trace of a reference arm. The housing can be the hollow guide wire of a catheter (858). The branches can be coupled to adjustable delays, for example ((830), $L_3$, $\tau_3$) ((834), $L_2$, $\tau_2$), and ((838), $L_1$, $\tau_1$)) (additional delays not shown). The catheter having guidewire (858) and optical head (846) can be inserted in an artery (854) using conventional medical procedures and the radial light into and backscattered from the sample (866), (870), (others not shown) from optical head (846) of the device used to detect a vulnerable plaque (862) covering a lipid (858) pocket in the artery (854). The number of fiber branches that can be placed inside the hollow guide wire (858) can vary and along with the dimensions of the waveguides, and will vary depending on the inside diameter of the guide wire or conduit used as a guide. The guide wire is a standard part of ordinary catheters and may chosen to be convenient for the cardiologists.

Rapid signal acquisition and data evaluation capability for longitudinal and radial inspection along a long artery may be achieved in a few seconds, for example it is expected that a 10 centimeter artery can be scanned in about 10-20 seconds using versions of the present invention. Several methods for deflection of light in the range of about 90° to the direction of light propagating along axis of the waveguide or plurality of optical fibers in a fiber bundle can be used in order to "look" at arterial walls. The small size of the waveguide and guide wire along with remote location of the reference section and detector can be used to provide a compact catheter with multiple-branch probes for catheter operation.

Characterizing arteries or other cavities and conduits for foreign material or growth would benefit from the ability to characterize the surfaces using radial scans of the cavity surface. For arteries one objective is to probe the arterial walls for vulnerable plaques. The tips of the probes can be made such that the output light propagated by the waveguides or fiber elements is directed toward the conduit walls or in the present case the arterial walls. As an example, the probe shown in FIG. 8(b) has six fibers ((818)-(828)) pointing in different radial directions. When this probe is used with an interferometer or autocorrelator with sufficient scanning range, all six LCI profiles can be obtained in one single trace or scan of the variable delay of the reference (interferometer) or delay compensator(autocorrelator) section, and these profiles separated from each other by virtue of the individual variable delays imparted to each branch by the methods described vide supra. The artery (854) shown in cross-section in FIG. 8(b) right illustrates a vulnerable plaque (862) protecting a lipid reservoir (858) just at branch location #3 for probe (818). In FIG. 8(c) an expected scan for the catheter in the artery (854) is illustrated showing the interference signals for each of the waveguides. All the profiles which correspond to healthy walls, profiles 1, 2, and 4-6 are shown to be identical. Profile #3 shows a trace that would be expected to corresponds to a vulnerable plaque consisting of a layer of calcified material (862) and a lipid pool (858) behind it within the arterial wall (854) detected by waveguide (818). The widths of the plaque and lipid regions are measures of their respective thicknesses. The scans illustrated in FIG. 8(c) can be digitized and the various profiles can be separated and stored in the computer memory for processing. The scans from each waveguide in the device may be digitized and compared to each other or a population of normal artery scans and used to diagnose the presence or absence, state, extent, or location of a lesion such as a vulnerable plaque, a tumor, or damaged tissue. The catheter may then be moved along the length of the conduit or artery and another radial scan taken and processed.

In another non-limiting example of a catheter illustrated in FIG. 9, the waveguide fibers (918)-(928) can be assembled around a thin solid and flexible central guide wire (966), such that the fiber assembly itself can act as its own guide. The outer surface of the waveguides can be enclosed for example using shrinkable latex or other polymeric and chemically compatible tubing (970). An internal guide wire is useful when a compact sensor is desired. It will be described further in connection with the geometry of the optical head (946).

As illustrated in FIG. 9(a), the various sample branches of an interferometer sensor, for example waveguides (918), (922), and (926), (additional waveguide branches (920), (924), (928), are illustrated in FIG. 9(b)) are brought together and placed inside a housing (970) covering a portion of two or more light propagating probe branches, the probes capable of guiding light from a low coherence source to a sample and guiding backscattered light from the sample to a reference section coupled via coupler or tree (914) to waveguide (910). Waveguide (910) may be coupled to other elements such as splitters, circulators, or source light. Each probe is shown having an optional adjustable delay, for example (930), (934), and (938) that can be used with a variable delay in one or more reference arms of the reference section to provide resolution of two or more low coherence interferometric signals from the sample arms (918), (922), and (926) with a single trace of a reference arm. The housing can be shrinkable latex or other chemically compatible and optically acceptable material (970). The branches can be coupled to adjustable delays, for example ((930), $L_3$, $\tau_3$) ((934), $L_2$, $\tau_2$), and ((938), $L_1$, $\tau_1$)) (additional delays not shown). The device having guidewire (966) and optical head (946) can be inserted in an artery (954) using conventional medical procedures and the radial light into and backscattered from the sample (972), (976), (others not shown) from optical head (946) of the device used to detect a vulnerable plaque (962) covering a lipid (958) pocket in the artery (954). The number of waveguides or fiber branches that can be placed inside the hollow guide wire (970) can vary and along with the dimensions of the waveguides, and will vary depending on the inside diameter of the guide wire or conduit used as a guide.

Allocating from between 1.5 mm and 2.0 mm per profile (depending on scattering property of sample), a single scan of the inner circumference of an artery would require 9 mm to 12 mm of travel and take approximately 600 milliseconds for 6 scans excluding rotation of the probe in the artery. In a system in a version of the present invention with a PZT drum and six probes, the same scan may take between 75 and 100 milliseconds (ms) to get a trace that contain profiles for all six locations. In operation, one inserts the catheter up to a particular location in the artery, and after the scan is recorded, the catheter is pulled back (automatically) by about one millimeter and the scan is repeated until the desired axial length is covered. A non-limiting automatic pulling rate of about 5 to 10 mm/s can be used. At such a rate, and with 100 ms per scan, it would be possible to examine a 10 cm length of artery in about 20 to 30 seconds with a version of the present invention compared to about 2-3 minutes with a probe having only a single fiber. Advantageously, the shorter scan and pulling time reduces stress on a patient during the procedure. Digitized scans for the various waveguide signals at each position along the artery can be made and stored in the computer memory for processing, analysis, or viewing.

One aspect in the system is that the instrument can be programmed to recognize a disease profile, for example profile #3 illustrated in FIG. 8(c). Profile shapes such as interference intensities as a function of light penetration depth for normal and abnormal conditions (growth, morphology, height, scattering) for a material or tissue can be stored in the memory of a processor that is electrically or optically connected to the detector. During use, the interference signal from each probe in the sensor can be compared to a reference material stored trace as well as an abnormal stored trace. Traces for each of the probes can be compared to stored values or traces for normal tissue, and a indication provided to a health care provider when an aberrant trace is detected. Normal tissue traces can be stored and a range or distribution of normal tissue compared to an acquired trace. Changes in the interference profile, for example intensity, shape, or a combination of these outside of a threshold, from the stored normal profile or from a stored abnormal profile can be used to indicate the presence of an abnormal condition. The system can also be directed to probe the abnormal position direction and ignore the others by programming the scan start and stop time, thus reducing the scan time in the above case to about $\frac{1}{6}^{th}$ of the normal scan time and save several seconds from the total probing time. The alternative, if using a single probe, would require the user to aim the probe in one direction, then rotate to the next direction until all directions are probed at a given point along the axis of the artery or other organ or conduit, then pull the catheter and repeat the process until the whole length of interest is probed.

Where an interferometer or autocorrelator includes an activating light source for photodymanic therapy, and where an abnormal trace is detected, the activating light may be directed to the probe(s) where the abnormal trace was detected. Alternatively, all of the probes can propagate the activating light to the region where the abnormal trace was detected. Photodymanic therapy can be performed and the progress of the therapy monitored by the probe after a treatment period.

Another advantage of the multiprobe system is that the cross-referenced profiles provide a natural averaging process to reduce speckle noise, and that the "wiggling" effect can be used to further reduce the speckle noise. Traditionally performing such averaging required repeating a given trace several times over a period of time and summing the traces together. For diagnosis of a tissue in a patient repeated measurements prolong the procedure and also introduce variation into the interference signal due to changes in patient body position, temperature and pressure. In the multiprobe versions of the present invention, such averaging is automatic and can be implemented for both an autocorrelator and an interferometer.

An optical head that propagates light from the waveguides of the sensor can be positioned at the distil end of a borescope, endoscope, or catheter. The optical head can be mounted or formed with the scope or waveguides and may be used to direct source light from the two or more waveguides of the sensor to the surface of the conduit or vessel. The optical head provides physical and chemical protection to the waveguides and may incorporate or be adjacent to a conduit in the device that provides fluid irrigation to the distil end of the sensor. Light in optical fibers is guided along the axis of the fiber. To aim the light at the wall of a conduit, a cavity, or a tissue such as an artery, light from the waveguides or fibers can be directed at an angle from the waveguide axis to the walls. Depending upon the orientation of the waveguide, mirror, or fiber end, the illumination of the sample with low coherence source light or the collection of backscattered light from the sample may occur at any angle with respect to the axis of the waveguide. For example, for viewing flat surfaces light may be directed and collected in approximately parallel orientation with respect to the fiber axis as shown in FIG. 7, or the source light may be deflected by an angle to the fiber axis as shown in FIGS. 8-10. For characterizing the walls of conduits and vasculature the source light can be directed at about 90° toward the wall surface. FIG. 10(a-d) show non-limiting ways to achieve this objective. It involves the use of a multi-faceted reflecting surface such as a prism (1006), (1054), (1058), and (1082) that can be for example either polished metal or reflection-coated glass which is made to rest on the edges of the waveguides or fibers. The waveguides, for example fiber (1018) with core (1016) and clad (1020), with flat polished tips, can be arranged in a circular or other geometric fashion around a thin guide (1012) or support wire and may be held together along the guide wire with some cement (for example sprayed on the guide) or epoxy, or some combination of both. In one embodiment, shown in FIG. 10(a), a thin-walled antireflection (AR) coated (to minimize reflection) transparent sleeve (1010) that may be glass is placed around the fibers (1014) and (1018) in the bundle. The space between the guide wire, the fiber, and the prism can be filled with epoxy (1022). The space between the fiber tip, the sleeve, and the prism may be filled with epoxy FIG. 10(c) (1064) and FIG. 10 (d) (1092) or it may not be filled with epoxy as illustrated in FIG. 10(a) by (1024) and FIG. 10 (b) by (1032). If the space is filled with epoxy, it can be placed for a short time in a vacuum chamber to remove air bubbles. An additional dome-shaped mass of epoxy (1026), (1046), (1062), or (1086) can be added to the tip of the assembly in order to prevent scarring the artery or other sensitive tissues/materials during catheter insertion.

The optical heads illustrated in FIG. 10 can be used for the interferometer multiple probe and the autocorrelator multiple probe. FIG. 10 (a-b) illustrate probe head configurations with flat tip fiber waveguides and reflecting prisms. FIG. 10(a) is for the interferometer, and 10(b) is for the autocorrelator. The difference between the interferometer and the autocorrelator fiber bundles is that partial reflectors, for example (1034) and (1036), and specific delays (1038) and (1042) are provided in each branch of the autocorrelator probe. These structures for the autocorrelator are illustrated in FIG. 10(b) as indicated by the fiber sections $L_1$ and $L_2$, and the partial mirrors between them and the main probe branches (1052) and (1056). These branches can be made by cleaving the main portion at the desired length for the reference light and depositing partial reflectors (1036) and (1034), preferably having about 33% reflection, at the cleaved fiber ends, an then fusing the extensions $L_1$ (1038) and $L_2$ (1042) to their respective branches.

FIG. 10(c) and FIG. 10(d) illustrate alternate heads which can be used for protecting the waveguides and directing source light to the sample. In these cases, an epoxy or other optically transparent material in the form of a cap is fashioned over the ends of the waveguides. The epoxy or other material can be ground and polished to remove rough edges and decrease the difference in size between the outer cap surface and the outside of the fiber bundle or housing conduit. The cap sides may have an antireflective coating (1066) or (1080) applied to the surface. These approaches provide a reasonably flexible stand-alone catheter which is capable of providing source light to the sample surface and collecting backscattered light from the surface. For characterizing vasculature and other narrow conduits with these sensors the cap provides about a 90° angle output and input, for example (1072) and (1096) others not shown, to the axis of the guide wire and the capped device does not damage an artery.

FIG. 11 illustrates additional non-limiting examples for deflecting light from the waveguide axis to the surface of the sample so that source light from two or more waveguides can be used to simultaneously characterize the sample. This can involve grinding and polishing the fiber tips at an angle and depositing a mirror coating on the angled fiber face (1126) in FIG. 11(a) and (1170) in FIG. 11(b). The fiber (1112) includes a cladding (1106) and core (1108). In FIG. 11(a) and (b) the angled fiber tip is illustrated by an approximately 45° angle made to the surface of the waveguide end. Similar to the previous approaches, the waveguide or fibers are arranged, preferably in an evenly distributed circular fashion around a thin guide wire (1114) and are held together along the guide wire with cement, epoxy, or both. In this case, the low coherence source light is emitted and backscattered light collected (1116) and (1118), others not shown, through the cladding (1104) and (1106) of the fibers (1110) and (1112) respectively. The curvature of the fibers can be shaped by laser machining or molding to act as a convex lens which provides some degree of collimation to the source light. The wall of the fiber can be AR-coated, for example (1102) and (1122) to minimize reflection. Portions of the space between the guide wire (1114) or (1134) and the fibers can be filled with epoxy (1130) or (1166) or other transparent and chemically inert material. No special treatment is needed for this epoxy, since no light is transmitted through it and there is also no specific alignment requirement. It is only sufficient to shape the tip in a shape to prevent damage to the sample or artery during insertion. The illustration of FIG. 11(a) is used in an interferometric sensor, while FIG. 11(b) illustrates multiple waveguides (1142) and (1138), others not shown, about a guide wire (1134), each waveguide having partial reflectors (1150) and (1152) and angled delay elements (1154) and (1158) which could be used in an autocorrelator. Source light to a sample and backscattered light collected from the sample (1160) is propagated by fiber (1138), while source light to a sample and backscattered light collected from the sample (1176) is propagated by fiber (1142).

With a light source of sufficient intensity, there is no fundamental limitation to the number of probe branches that can be used. Thus, with enough probes, it is possible to obtain LCI traces around the circumference of a hollow sample and along its length as well. The waveguides or fibers can be distributed about a guidewire or within a housing, preferably they are distributed to provide substantially uniform coverage or sampling of the material to be monitored. In certain applications, the allowable diameter of the probe may be quite small and the number of waveguides determined by the allowable size of the probe. More specifically in the case of human arteries, the overall probe diameter may be required to be of the order of 0.5 mm or less. FIG. 12 shows several configuration for fiber optical probes having 3, 4, 5, and 6 branches. These configurations can be obtained by placing the center of the fibers on vertices of appropriate polygons, circles, or ellipses, and deriving formulas for housing waveguides around them in terms of the fiber clad diameter. FIG. 12(b) illustrates that for the four fibers 1202, 1204, 1206, and 1208 with diameter $D_f$ in housing 1218, a close packed configuration for the fibers in this housing configuration the may be achieved using guidewire of diameter $D_g$ and housing diameter $D_p$. Examples of formulas are given in FIG. 12 and formulas can also be derived for the diameter of their supporting guide wire. Although preferred, the various embodiments of the present invention are not limited to close packed configurations. Also, similar waveguide configurations could be derived for irregularly shaped housings. The number of waveguides in the guidewire can also vary with the limit of the guidewire diameter and requirements for flexibility of the scope and in particular for a catheter. The diameter for a catheter or borescope or endoscope can be chose so that it fits through the smallest hole available to access the cavity. The borescope diameter preferably clears the sides of the hole or organ into which it is inserted. The length of the endoscope or borescope can be chosen to penetrate to the greatest depth required, but not so long as to be unwieldy outside the hole.

The point of borescope, catheter, or endoscope entry and the area to be examined can be used to modify the direction of view that a reflecting prism can be fashioned to direct the source light. If the subject is straight ahead of an entry hole an approximately 0° direction-of-view can be used and information from two or more fibers used to scan an area of the surface. If the surface or material to be viewed is very close to the entry port of the borescope or endoscope, like engine valves near a spark plug hole, a backward-looking prism or suitably angled and coated optical fiber may be used. For conduits like an colon or bore of a rifle barrel, a head having a 90° reflecting prism (90 degrees to the axis of the fiber or scope axis) can be used.

Field-of-view from the borescope or endoscope time may range from 10 to about 90 degrees and can be chosen based on the distance from the distal end of the borescope to the subject. A borescope, can have has a very large depth of field which can be from infinity down to an centimeter or less. Borescopes and endoscopes of the present invention may be rigid or flexible and can use but are not limited to fiber optic illumination to carry light from an external light source through a flexible light guide, then through the borescope, to the distal end. Other sources of illumination may include activating light for photodynamic therapy, or a bulb at the tip or light emitting diodes.

In FIG. 12, $D_p$, $D_f$, and $D_g$ represents the diameter of probe (the circle around the fibers) or sample arm, the diameter of the fiber, and the diameter of the guide wire, respectively. Various non-limiting configurations for a typical fiber having 125-micron clad diameter are illustrated in Table 1.

TABLE 1

Relation of probe and guide wire diameters to fiber diameter.
Application to fiber with $D_f$ = 125 micron

| Number of probe branches | Overall probe diameter $D_p$ (and actual value) | Guide wire diameter $D_g$ |
|---|---|---|
| 3 | $D_p = 2.15\, D_f$ (269 μm) | $D_g = 0.15\, D_f$ (19 μm) |
| 4 | $D_p = 2.41\, D_f$ (301 μm) | $D_g = 0.41\, D_f$ (51 μm) |
| 5 | $D_p = 2.7\, D_f$ (338 μm) | $D_g = 0.7\, D_f$ (88 μm) |
| 6 | $D_p = 3.0\, D_f$ (375 μm) | $D_g = 1.0\, D_f$ (125 μm) |

In an autocorrelator in versions of the present invention, the sensing light in a given branch can interfere with the reference lights from other branches to provide several replica of the LCI signal for that particular branch. These signals can be made to superimpose by equalizing the various paths, which causes the various replicas add to the self-referenced LCI to increase the total signal or provide an average signal without the need to repeat scans. A small modulation can be added to vary $d_1$-$d_2$ so that it is not zero, modulating them about the self-referenced signal, and achieve noise reduction by averaging the noise out. The same result can be achieved with an interferometer by the use of two or more reference arms.

FIG. 13 shows the interferometer previously described in FIG. 4, but with the addition of an second reference arm (1314) having variable delay (1342) of $L_b$, $\tau_b$ and adjustable mirror (1332) in addition to the first reference arm (1310) having variable delay (1328) of $L_a$, $\tau_a$ and adjustable mirror (1330). Low coherence light from source (1306) with optional isolator (1308), propagates through waveguide (1312) to splitter (1316). A portion of the source light from the splitter enters the reference arms through waveguide (1324) and the other portion enters the tree (1344) through waveguide (1348) where it is propagated to the sample arms (1318), (1322) and other arms (1340) (not shown). Sample arm (1318) has variable delay (1334) of $L_1$, $\tau_1$ and sample arm (1322) has variable delay (1336) of $L_2$, $\tau_2$, (the delays of the other arms are not shown). Source light backscattered from the sample (1338) is propagated by the sample arms and combined with the reference light and propagated to the detector through waveguide (1320) coupled to splitter (1316). The interference measured at the detector can be processed further by processor (1356).

The analysis for the sensor of FIG. 13 can be done for an arbitrary number of reference and sensing arms, but two reference arms (1310) and (1314) and sensing or sample arms (1318), (1322), and others (1340) are used to illustrate the operation in this case. The sensing electric fields can be designated as $E_{s1}$ and $E_{s2}$ as before, and the two reference fields designated as $E_{ra}$ and $E_{rb}$, respectively. Carrying the analysis and selecting the detector current components which provide matching path lengths, for example path length differences which can be made equal to zero, yields the following four signal components: $i_{s1a}$, $i_{s1b}$, $i_{s2a}$, and $i_{s2b}$ as shown in equations (20)-(23)

$$i_{s1a}(z) = \sqrt{I_{ra} I_{s1}(z)}\, \exp\left[-\left(\frac{\Delta_{1a}}{L_c}\right)^2\right] \cos\left(\frac{2\pi \Delta_{1a}}{\lambda_o}\right), \quad (20)$$

where $$\Delta_{1a} = nL_a - (nL_1 + n_s z)$$

$$i_{s1b}(z) = \sqrt{I_{rb} I_{s1}(z)}\, \exp\left[-\left(\frac{\Delta_{1b}}{L_c}\right)^2\right] \cos\left(\frac{2\pi \Delta_{1b}}{\lambda_o}\right), \quad (21)$$

where $$\Delta_{1b} = nL_b - (nL_1 + n_s z)$$

$$i_{s2a}(z) = \sqrt{I_{ra} I_{s2}(z)}\, \exp\left[-\left(\frac{\Delta_{2a}}{L_c}\right)^2\right] \cos\left(\frac{2\pi \Delta_{2a}}{\lambda_o}\right), \quad (22)$$

where $$\Delta_{2a} = nL_a - (nL_2 + n_s z)$$

$$i_{s2b}(z) = \sqrt{I_{rb} I_{s2}(z)}\, \exp\left[-\left(\frac{\Delta_{2b}}{L_c}\right)^2\right] \cos\left(\frac{2\pi \Delta_{2b}}{\lambda_o}\right), \quad (23)$$

where $$\Delta_{2b} = nL_b - (nL_2 + n_s z)$$

where $I_{ra} = E_{oa}^2$, $I_{rb} = E_{ob}^2$, $I_{s1} = E_{s1}^2$, $I_{s2} = E_{s2}^2$.

There is an extra DC term (included because its path difference can be made equal to zero) which carries no information:

$$I_{ab} = \sqrt{I_{ra} I_{rb}}\, \exp\left[-\left(\frac{\Delta_{ab}}{L_c}\right)^2\right] \cos\left(\frac{2\pi \Delta_{ab}}{\lambda_o}\right), \quad (24)$$

where $$\Delta_{ab} = n(L_a - L_b)$$

Comparing these equations, it can be shown that $i_{s1a}(z)$ and $i_{s1b}(z)$ are both LCI signals for $I_{s1}(z)$, and that $i_{s2a}(z)$ and $i_{s2b}(Z)$ are LCI signals for $i_{s2}(z)$ Therefore, they can be combined, respectively, to give $i_{s1}(z)$ and $i_{1s2}(z)$, where $$i_{s1}(z) = i_{s1a}(z) + i_{s1b}(z) \text{ and } i_{s2}(z) = i_{s2a}(z) + z_{s2b}(z) \quad (25)$$

In particular, the two terms in $i_{s1}(z)$ and the two terms in $i_{s2}(z)$ add up exactly if $L_a = L_b$. Furthermore, if a slight random time modulation at a frequency higher than the scan rate is imparted to $L_b$, then $i_{s1b}(z)$ will wiggle around $i_{s1a}$, and $i_{s2b}$ will wiggle around $i_{s2a}$. The two components of each signal will wiggle in opposite directions about each other if the modulation imparted to $L_a$, is the opposite of that imparted to $L_b$. In general, any variation of $L_a$ and $L_b$ are allowed. Again, since the LCI signal is peak-detected, the phase information is lost by the wiggling process and the speckle noise is averaged out.

EXAMPLE 1

This prophetic example illustrates how an version of the present invention can be used for detecting plaque within the coronary or other patient vasculature. The apparatus and techniques could also be applied to characterizing lesions in other body lumens which are associated with various disease conditions. The methods and apparatus can be implemented within the body lumen to identify diseased tissue or monitor the course of treatment for a particular condition. The apparatus is able to interrogate the body lumen over a relatively long distance to characterize the tissue in an efficient fashion by providing interferometric information on the tissue from multiple probes in a single sweep of a variable delay of the apparatus.

Coronary artery disease resulting from the build-up of atherosclerotic plaque in the coronary arteries is a leading cause of death. The build-up of plaque causes a narrowing of the artery, commonly referred to as a lesion, which reduces blood flow to the myocardium (heart muscle tissue). Myocardial infarction can occur when an arterial lesion abruptly closes the vessel, causing complete cessation of blood flow to portions of the myocardium. Even if abrupt closure does not occur, blood flow may decrease resulting in chronically insufficient blood flow which can cause significant tissue damage over time.

Plaques which form in the coronaries and other vessels comprise inflammatory cells, smooth muscles cells, cholesterol, and fatty substances, and these materials are usually trapped between the endothelium of the vessel and the underlying smooth muscle cells. It is expected that these lesions will have optical properties that differ from the surrounding healthy tissue. The difference in the optical properties may be detected and characterized by a change in incident source light of one or more wavelengths backscattered from the sample. Depending on various factors, including thickness, composition, and size of the deposited materials, the plaques can be characterized as stable or unstable. The plaque is normally covered by a cap and/or an endothelial layer as illustrated in FIG. 8($b$). When the cap and/or endothelial layer is disrupted, the ruptured plaque releases highly thrombogenic constituent materials which are capable of activating the clotting cascade and inducing rapid and substantial coronary thrombosis. Such plaque is referred to as unstable or vulnerable, and the resulting thrombus formation can cause unstable angina chest pain, acute myocardial infarction (heart attack), sudden coronary death, and stroke. Based upon the light backscattered source light of one or more wavelengths from the artery walls, the sensor of the present invention may be used to determine the location, chemical and physical properties, and nature of the lesion in an artery. This information can be used to facilitate determining whether the plaque is stable or unstable, and may be used to treat and monitor the treatment.

As shown in FIG. 14, a sensor for characterizing the artery can be made by coupling three waveguides (1408), (1428), and (1442) using tree coupler (1414), each waveguide having an adjustable delay such as (1410), (1416), (1420) the waveguides located within a housing (1418). The pathlength of the three waveguides differ from each other and are less than the pathlength of the delay compensator section. The waveguides a can be coupled to a low coherence light source (not shown) and a delay compensator section through a circulator (1426). The delay compensator section (1430) includes waveguide (1444) and an adjustable delay (1464) and waveguide (1448) and adjustable delay (1458). Probe waveguide (1428) is shown with partial reflector (1422) and delay element (1424); the other probe arms (1408) and (1442) also include these elements. The delay arms (1444) and (1448) are coupled to Faraday reflectors (1446) and (1450) respectively. The sensor waveguides are able to propagate light input (1412) from one or more low coherence sources (not shown) through waveguide (1404) coupled to the circulator (1426) and to a sample tissue such as an artery (1454) through probe waveguides (1408), (1442), and (1428). The low coherence light is directed to the surface of the sample artery (1454) and backscattered light from the surface collected by the one or more probes (1438). These probe waveguides are able to propagate backscattered source light from the sample (1438), to an interferometer or delay compensator section (1430) through waveguide (1432) and splitter (1436). The waveguides (1408), (1442), and (1428) are configured such that interference between the backscattered light from the sample (1458) and reference light from the probe arms is separately detected by a detector, not shown, which can be coupled to the splitter (1436) through waveguide (1452). The three waveguide interference signals are detected during a single sweep of the delay compensator section adjustable delays ±L or ±τ.

The artery or other tissue (1454) can be characterized by contacting it as illustrated in FIG. 14. The sensor probe and reference section are coupled together and each probe arm has an adjustable delay that can be used to adjust the delay of the probes (1408), (1442), and (1428) to account for index of refraction (n) changes, light penetration depth (z), and keep the length of the probes different from one another and within the adjustable delay of the delay compensator section. Interference between backscattered source light from the sample (1454) detected by the three probe arms combined with reference light from the probe arms interfere after compensation by the delay compensator section and the interference signal measured at a detector. The interference signals are resolved during a single trace of the reference section where a trace is at least the sum of the nL's for each probe and nz for each probe.

The interference signal determined for each probe arm could be completely separated from the LCI signal from the other probe arms or it could be less than completely separated. Adjustment to the probe arm delays can be made to achieve complete separation. In FIG. 14, the interference detected for each of the three probes provides a characterization of the artery in the three sections. A change in the interference measured by any of the probes that differs from one or more of the other probes or from a reference trace from a healthy artery is expected to indicate a change in the health or state of the tissue. For a patient at risk for having lesions based upon past medical diagnosis, previous medical condition, or present health as determined by a physician, the presence of an abnormal interference pattern from a scan may indicate the presence of a diseased tissue such as a plaque in the artery. By using one or more low coherence light sources with different center wavelength, a spectroscopic analysis of a tissue or sample can be performed and the trace as a function of wavelength determined. It is expected that because the penetration and backscattering of low coherence light varies with wavelength and tissue type, variations in LCI signals between normal and diseased tissue can be readily detected. Other methods may be used to confirm the presence of a diseased tissue like a vulnerable plaque and support that a particular trace structure indicates the presence of a diseased tissue like a vulnerable plaque.

This example illustrates how detecting the interference between low coherence light backscattered from a sample that is propagated in two or more adjustable waveguides can be combined with low coherence light from a delay compensator section having an adjustable delay so that a single sweep of the reference section yields interference signals that are resolved and provide information about a tissue.

EXAMPLE 2

This prophetic example illustrate how a sensor of the present invention may be used in photodynamic therapy to treat and monitor a lesion.

Photodynamic therapy (PDT) is effective in destroying diseased tissue and tumors using light that is absorbed by a photoreactive agent administered to the patient. The photoreactive agent is selectively preferentially absorbed by or linked to the abnormal or diseased tissue and has a characteristic absorption wavelength or absorption band that activates the agent. When activated by the light, the photoreactive agent can produce compounds that destroy the abnormal tissue. The depth of light penetration, and consequently of the tissue necrosis, is a function of light wavelength, and is typically less than one centimeter.

PDT may be administered locally to a site in or on a patient using light from an external light source such as a laser that is coupled to a plurality of optical fibers or waveguides. The waveguides that propagate the light to the site can be housed in a catheter or endoscope and these same waveguides can also be the sample arms of an autocorrelator or interferometric sensor. Alternatively, the catheter or endoscope houses separate sets of waveguides—one set to propagate light for photodynamic therapy to a site of the patient's body to be treated, another set of waveguides acting as sample or probe arms for the sensor.

The sample arms of an autocorrelator or interferometric sensor can be used to locate a lesion and can be used to monitor the progress of the photodynamic therapy including damage to abnormal and normal tissue. Damage to normal tissue can occur during PDT due to the non-homogeneous distribution or non-selective binding of the photoreactive agent within an abnormal tissue and within the surrounding normal tissue.

For example, a catheter that houses two or more sample arms can be inserted within the diseased tissue at a site as illustrated in FIG. 15. In this non-limiting example, light from multiple wavelength sources (1510) $\lambda_1$, (1512) $\lambda_2$, and (1514) $\lambda_3$ can be multiplexed using wavelength division multiplexer (1522) coupled into circulator (1530). Light for activating an agent from source (1516) $\lambda_4$ may be coupled through wave division multiplexer (1522) into the circulator (1530) or one of the low coherence sources may act as an activating light. Alternatively, a light source can be disposed outside of the patient's body (not shown) while administering the light therapy and a catheter or endoscope including one or more sample arms (1540), (1542), or (1544) at or near the site to monitor the photodynamic therapy. Where the light source is located outside of the patient's body, and if necessary, the source is selected to have wavelengths and intensity sufficient to penetrate normal tissue overlying the internal treatment site to reach the diseased tissue.

Photodynamic therapy can include the acts of activating a photosensitive agent administered to the patient and monitoring the normal and disease tissue at the site where the light is directed with a sensor or catheter of the present invention having two or more sample or probe arms. For example, activating light from source (1516) can be directed through WDM (1522), through circulator (1530) and propagated into tree (1534) where it is divided into waveguides (1540), (1542), and (1544) and directed to the distal end of a catheter adjacent tissue as illustrated in FIG. 15. Alternatively, the activating light may be directed to a single one of the waveguides (1540), (1542), and (1544) using an optical switch (not shown). Each of the probe arms can have an adjustable delay (1556), (1560), and (1562), and each includes partial reflector such as (1566) and delay element (1564). After a period of exposure of the site to the activating light from source (1516), the source can be turned off and the site characterized by directing low coherence light from one or more sources like (1510), (1512), or (1514) to the sample arms of the sensor in the catheter housing (1552). A phototherapy method according to another aspect of the invention includes the acts of identifying a tissue in need of photodynamic therapy using a sensor of the present invention having one and preferably two or more sample arms and one or more reference arms, and activating a pharmaceutical composition administered to the patient that can be activated by light flux and that leads to necrosis of the identified tissue in response to the light flux. The method can further include the act of interferometric monitoring of the progress of the photodynamic therapy. Light flux for activating the pharmaceutical can be applied externally to the patient, or it can be applied to any tube-like anatomical organ, duct, or cavity, including, but not limited to, esophagus, blood vessels, lymphatics, urethra, lung/trachea, cervix, oral cavity, and rectum of the patient through a catheter. The catheter, which may be introduced into the conduit or vessel directly, or by penetration through tissue, such as muscle tissue, as by means of a needle, preferably is a catheter having one or more, and even more preferably two or more sample arms of an interferometer or autocorrelator of the present invention. Based on the information received from the sensor, the therapy may be modified including but not limited to changing the intensity or flux of the light applied to the tissue and or changing the duration of the light applied to the site.

The results of this example show that versions of the present invention may be used to identify a tissue in need of treatment, may be used to provide treatment, and can be used to monitor the progress of a therapy.

EXAMPLE 3

This example illustrates a method for characterizing a material sample that includes contacting the material with a sensor having two or more probes or sample arms and a delay compensator or a reference section respectively. Each probe arm can include an adjustable delay, the probe arms and reference section configured such that an interference between backscattered source light from the sample for two or more probe arms and reference light occurs and is detected during a single trace of the delay compensator or reference section.

Preferably the interference signal for the two or more probe or sample arms are at least partially separated from each other. The material can be a tissue where characterization includes the detection of a disease state of the tissue. Preferably the disease state being characterized is a vulnerable plaque.

EXAMPLE 4

This prophetic example illustrates a method of making a sensor in versions of the present invention;

The sensor can be made by coupling two or more waveguides sample arms and one or more reference arms having adjustable delays, the waveguides able to propagate light from a low coherence source to a sample and able to propagate backscattered source light from the sample. The waveguides can be configured such that interference between the backscattered light and reference light for two or more waveguides are separated from each other during a single sweep of a variable delay of a reference section or a single sweep of adjustable delay of a delay compensator section.

Backscattered light collected from two or more probes or sample arms may be coupled to a reference section or to a delay compensator section. Interference between the backscattered light and reference light is measured by a detector that can be coupled to a splitter propagating light from reference arm or the delay compensator. The interference measured by a detector can be sent to a processor, the detector output is proportional to the interference and a signal or display provided by the processor.

Although the present invention has been described in considerable detail with reference to certain preferred embodiments thereof, other versions are possible. Therefore the spirit and scope of the appended claims should not be limited to the description and the preferred versions contain within this specification.

What is claimed is:

1. A sensor comprising:
   two or more probes arms capable of being coupled to a low coherence light source, each probe arm propagating reference light and propagating backscattered light from the sample, each probe partially reflecting the source light; and
   a delay compensator coupled to the probe arms to receive reference and backscattered light from the probe arms, the delay compensator having polarization maintaining reflectors and a variable delay between the arms, where the delay compensator brings the interference between the reference light and backscattered light to within the coherence length of the light source.

2. The sensor of claim 1, where the delay arms are coupled to a port of a circulator and the probes arms are coupled to a second port of the circulator, the circulator propagating the backscattered light and the reference light from the probes to the delay compensator.

3. The sensor of claim 1, where arms of the delay compensator are configured so that the interference between the reference and backscattered source light occurs under the gating function of the delay compensator.

4. The sensor of claim 1, further including a detector coupled to the delay compensator, the detector measuring the interference between the light reflected from the delay arms.

5. The sensor of claim 4, where the detector connected to a processor that provides an output proportional to the interference between the light reflected from the delay arms.

6. The sensor of claim 1, where the one or more probes has a delay that is modulated to reduce noise.

7. The sensor of claim 1, further including a housing.

8. The sensor of claim 1, further including one or more a low coherence light sources.

9. The sensor of claim 1, further including an activating light source.

10. An apparatus comprising:
    a housing covering a portion of two or more light propagating probes, the two or more probes arms capable of being coupled to a low coherence light source, each probe arm propagating reference light and propagating backscattered light from the sample, each probe partially reflecting the source light, the two or more probes capable of directing light to a sample; and
    a delay compensator having two arms receiving reference and backscattered light from the probe arms, the delay compensator having polarization maintaining reflectors and a variable delay between the arms, where the delay compensator brings the interference between the reference light and backscattered light to within the coherence length of the light source.

11. The apparatus of claim 10, having an optical head that directs light from the two or more probes to the sample.

12. The apparatus of claim 10, where the probes are optical fibers.

13. The apparatus of claim 10, wherein the housing is a catheter.

14. The apparatus of claim 10, where the probes include an internal reflector.

15. The apparatus of claim 10, where the apparatus has a guidewire.

16. The apparatus of claim 10, capable of being coupled to a detector and low coherence light source.

17. The apparatus of claim 10, further including one or more low coherence light sources coupled to the probes and reference section and a detector coupled to the apparatus for measuring the interference between the backscattered light in the two or more probe arms and reference light.

18. The apparatus of claim 10, further including an activating light source.

* * * * *